United States Patent [19]

Ho et al.

[11] Patent Number: 5,178,865
[45] Date of Patent: Jan. 12, 1993

[54] CHINESE HERBAL EXTRACTS IN THE TREATMENT OF HIV RELATED DISEASE IN VITRO

[75] Inventors: David D. Ho, Chapqua, N.Y.; Xiling S. Li, Alhambra, Calif.

[73] Assignee: Cedars-Sinai Medical Center, Los Angeles, Calif.

[21] Appl. No.: 712,062

[22] Filed: Jun. 7, 1991

Related U.S. Application Data

[63] Continuation-in-part of Ser. No. 540,158, Jun. 19, 1990, abandoned.

[51] Int. Cl.$^5$ .......................... A61K 35/78; C12Q 1/70
[52] U.S. Cl. ................................ 424/195.1; 514/783; 435/5
[58] Field of Search ...................... 424/195.1; 514/783; 435/5

[56] References Cited

U.S. PATENT DOCUMENTS

| | | | |
|---|---|---|---|
| 98,535 | 1/1870 | Willis | 424/195.1 |
| 241,144 | 5/1881 | Lange | 424/195.1 |
| 308,900 | 12/1884 | Kieffer | 424/195.1 |
| 4,469,685 | 9/1984 | Kojima | 424/195.1 |
| 4,869,903 | 9/1989 | Lifson et al. | 424/195.1 |
| 4,885,235 | 12/1989 | Osther | 435/5 |
| 4,886,665 | 12/1989 | Kovacs | 424/195.1 |
| 4,906,470 | 3/1990 | Liu | 424/195.1 |
| 4,937,074 | 6/1990 | Venrateswaran | 424/195.1 |

OTHER PUBLICATIONS

Steinmetz, E. F. Codex Vegetabilis Amsterdam, 1957.
McCormick, J. B. et al., Ribavirin Suppresses Replication Of Lymphadenopathy-Associated Virus In Cultures of Human Adult T Lymphocytes, Lancet, 8429:1367-1369, Dec. 15, 1984.
Ho, D. D. et al., Recombinant Human Interferon Alfa-A Suppresses HTLV-III Replication In Vitro, Lancet, 8426:602-604, Mar. 16, 1985.
Mitsuya, H. et al., 3'-Azido-3'-deoxythymidine (BW A509U): An Antiviral Agent That Inhibits The Infectivity And Cytopathic Effect Of Human T-Lymphotropic Virus Type III/Lymphadenopathy-Associated Virus In Vitro, Proc. Natl. Acad. Sci., 82:7096-7100 (1985).
Sandstrom, E. G. et al., Inhibition Of Human T-Cell Lymphotropic Virus Type III In Vitro By Phosphonoformate, Lancet, 8444:1480-1482, Jun. 29, 1985.
Pert, C. B. et al., Octapeptides Deduced From The Neuropeptide Receptor-Like Pattern Of Antigen T4 In Brain Potently Inhibit Human Immunodeficiency Virus Receptor Binding And T-Cell Infectivity, Proc. Natl. Acad. Sci., 83:9254-9258 (1986).
Anand, R. et al., Rifabutine Inhibits HTLV-III, Lancet, 8472:97-98, Jan. 11, 1986.
Balzarini, J. et al., Comparative Inhibitory Effects Of Suramin And Other Selected Compounds On The Infectivity And Replication Of Human T-Cell Lymphotropic Virus (HTLV-III)/Lymphadenopathy-Associated Virus (LAV), Int. J. Cancer, 37:451-457 (1986).

Primary Examiner—Johnnie R. Brown
Assistant Examiner—Ralph Gitomer
Attorney, Agent, or Firm—Lyon & Lyon

[57] ABSTRACT

The invention features herbal extracts from ten (10) Chinese Herbal Medicines demonstrating significant in vitro and ex vivo anti-HIV activity and their use for the diagnosis and treatment of HIV and HIV-related disease.

20 Claims, 18 Drawing Sheets

CHINESE HERBAL EXTRACTS IN THE TREATMENT OF HIV RELATED DISEASE IN VITRO

This application is a continuation-in-part of copending U.S. application Ser. No. 07/540,158, filed Jun. 19, 1990, now abandoned.

TECHNICAL FIELD

This invention is in the fields of medicine and pharmacology. In particular, the invention features ten (10) commercially available Chinese Herbal Extracts (CHEs) exhibiting in vitro and/or ex vivo activity against the etiologic agent of Acquired Immune Deficiency Syndrome (AIDS) and AIDS related complex (ARC).

BACKGROUND ART

Acquired Immune Deficiency Syndrome is a pandemic immunosuppressive disease which results in life threatening opportunistic infections and malignancies. A retrovirus, designated human immunodeficiency virus (HIV-1(HTLV-III LAV)), has been isolated and identified as the etiologic agent of this disease. This virus has been shown to be harbored by T helper lymphocytes and monocyte-macrophages, and it is detectable in whole blood, plasma, lymphatic fluid, serum, semen, saliva and central nervous system tissue. Ho et al., *New England Journal of Medicine,* 321:1621-1625 (1989). Although cells of the monocyte-macrophage lineage serve as important reservoirs of HIV infection, most of the cell-associated virus in the blood is contained within CD4+ T cells. Characteristically, then, AIDS is associated with a progressive depletion of T cells, especially the helper-inducer subset bearing the OKT4 surface marker.

Several agents have been reported to inhibit the growth of the human immunodeficiency virus in vitro. Among the agents exhibiting in vitro anti-HIV activity, some are now in clinical use, including ribavirin, zidovudine (AZT), the 2', 3'-dideoxynucleosides (DDI and DDC); ganciclovir alpha-interferon, interleukin-2, ampligen and isoprinosine. Anand et al., *Lancet* i,97-98 (1986); Balzarini et al., *Int. J. Cancer* 37:451-457 (1986); Ho et al., *Lancet,* i,602-604 (1985); McCormick et al., *Lancet* ii,1367-1369 (1984); Mitchell et al., *Lancet* i,8-90-892 (1987); Mitsuya et al., *Proc. Natl. Acad. Sci. USA* 83:1911-1915 and 82:7096-7100 (1985, 1986); Mitsuya et al., *Science* 226:172-174 (1984); Pert et al., *Proc. Natl. Acad. Sci. USA* 83:9254-9258 (1986); Pizzi et al., *Human Biol.* 22:151-190 (1950); Rozenbaum et al., *Lancet* i,4-50-451 (1985); Sandstrom et al., *Lancet* i,1480-1482 (1986); Veno and Kino, *Lancet* i,1379 (1987); Yamamoto et al., *Interferon Res.* 6:143-152 (1986), and *Antiviral Research* 7:127-137 (1987). However, no therapy to date is known to cure AIDS.

The majority of the compounds tested for use against HIV. including those referenced above, appear to be either too toxic for prolonged use or incapable of completely eliminating HIV infection from the human host. Blanche et al., *Lancet* i,863 (1986); De Clercq et al., *J. Med. Chem.* 29:1561-1569 (1986); Yarchoan et al., *Lancet* i,575-580 (1986); Wetterberg et al., *Lancet* i,159 (1987). In view of the severity of the AIDS situation and the toxicity and limited clinical efficacy of the compounds tested thus far, the scientists of the present invention have begun investigating the anti-HIV activity of extracts from Chinese medicinal herbs. Chang and Yeung, *Antiviral Research* 9:163-176 (1988); Chang et al., *Antiviral Research* 11:263-73 (1989). This interest in Chinese herbs was prompted by Chinese folklore, wherein a number of these herbs have been reputed to have anti-infective activity and to be well tolerated by humans. A subset of these herbs now also appear to exhibit anti-HIV activity, and are disclosed herein.

However, Chinese folk medicine is based largely on anecdotal observations spanning the past several thousands of years. Hence, the effectiveness of the medicinal herbs used by folk medicine practitioners has, for the most part, not been substantiated by scientific methods. Despite this lack of scientific proof, it is quite possible that some herbal remedies may have specific therapeutic action, as was proven to be the case with the antimalarial. qinghaosu, and perhaps even anti-HIV activity. Klayman, *Science,* 228:1049-1055 (1985). Consequently, with regard to the possible anti-HIV activity among Chinese herbal extracts, an urgent need exists for: 1) the identification of effective anti-HIV herbal extracts, 2) the substantive documentation, by modern scientific methods, of the effectiveness of these herbal extracts against HIV, and 3) the identification of effective anti-HIV Chinese herbal extracts that are less toxic than the currently available anti-HIV agents. The present invention satisfies this need and provides related advantages as well.

The papers cited throughout this application are incorporated herein by reference.

DISCLOSURE OF THE INVENTION

A total of fifty-six (56) herbal extracts. some of which are known to have anti-infective properties and to be non-toxic in clinical use in China, were screened for their anti-HIV activity using in vitro techniques. Of these fifty-six (56) herbal extracts, ten (10) were shown to have potent anti-HIV activity in in vitro experiments, and two (2) of these ten (10) also exhibited anti-HIV activity in ex vivo experiments.

These ten (10) include the extracts from: Sample #1—*Coptis chineusis*, which can be located in Western, Southern and Central China; Sample #8—*Ligusticum wallichii*, which can be found in Northern and Southwestern China, and *Salvia miltiorrhiza*, which can be located in most areas of China; Sample #21—*Illicium lanceolatum*, which can be located in Eastern and Southern China; Sample #30—*Isatis tinctoria*, which can be found in Central China, *Lonicera japonica*, which can be located in most areas of China, and *Polygonum bistorta*, which can be located in Northern, Eastern and Southwestern China; Sample #32—*Salvia miltiorrhiza*, which can be located in most areas of China; Sample #35—*Erycibe obtusifolia*, which can be found in Southern China, Taiwan, Japan, Indonesia and Northern Australia; Sample #39—*Acanthopanax graciliatylus*—which can be located in Central and Southwestern China and the Philippines; Sample #41—*Bostaurus domesticus*, which can be found in most areas of China and in Southern Africa, and *Scutellaria baicaleusis*, which can be located in Northern, Western and Central China and Southern Africa; Sample #44—*Inula helenium*, which can also be located in most areas of Northern China, and *Salvia miltiorrhiza*, which can be located in most areas of China; and Sample #49—*Lonicera japonica*, which can be located in most areas of China, and *Scutellaria baicaleusis*, which can be located in Northern, Western and Central China, as well as in Southern Africa. This information is reproduced in Table I below, which also provides alternative means for identifying the subject herbs.

TABLE I

| SAMPLE | NAME OF HERB | CLASSIFICATION | MAJOR LOCATION |
|---|---|---|---|
| #1 | *Coptis chineusis* Franch | Ranunculaceae | Western, Southern and Central China |
| *#8 | *Ligusticum wallichii* Franch and | Umbelliferae | Northern and Southwestern China; |
|  | *Salvia miltiorrhiza* Bunge | Labiatae | Most areas of China |
| #21 | *Illicium lanceolatum* A. C. Smith or *Illicium henryi* Diels | Illiciaceae | Eastern and Southern China |
| *#30 | *Isatis tinctoria* L. or *Isatis indigotica* Fort., | Cruciferae | Central China |
|  | *Lonicera japonica* Thunb and | Caprifoliaceae | Most areas of China |
|  | *Polygonum bistorta* L. | Polygonaceae | Northern, Eastern and Southwestern China |
| #32 | *Salvia miltiorrhiza* Bunge | Labiatae | Most areas of China |
| #35 | *Erycibe obtusifolia* Benth | Convolvulaceae | Southern China, Taiwan, Japan, Indonesia and Northern Australia |
| #39 | *Acanthopanax graciliatylus* W. W. Smith | Araliaceae | Central and Southwestern China, Philippines |
| *#41 | *Bostaurus domesticus* Gmel. and | Bovine choleic | Most areas of China |
|  | *Scutellaria baicaleusis* Georgi | Labiatae | Northern, Western and Central China, S. Africa |
| *#44 | *Salvia miltiorrhiza* Bunge and | Labiatae | Most areas of China |
|  | *Inula helenium* L. | Compositae | Northern, Northeastern and Northwestern China |
| *#49 | *Lonicera japonica* Thunb and | Caprifoliaceae | Most areas of China |
|  | *Scutellaria baicaleusis* Georgi | Labiatae | Northern, Western and Central China, S. Africa |

*A compound comprising more than one (1) herb.

In the context of the present specification, CHE is used to refer to any species of any of the herbs delineated above which, upon extraction, yields a fraction comprising a pharmacologically active agent, whether a component, a combination of components, a biological metabolite, a derivative thereof or a combination of the above, that exhibits in vitro and/or ex vivo anti-HIV activity. Since the precise chemical composition and pharmacologic mechanism of the CHEs has not yet been elucidated, it is possible that the anti-HIV activity may be due to a single CHE component, a combination of CHE components, or the biologic metabolite or derivative thereof.

By the terms "HIV," and "AIDS-related virus" is meant the commonly designated HIV series (human immunodeficiency virus) formerly called HTLV, LAV and ARV, and species thereof, as described in the incorporated references.

Similarly, the terms "HIV-related disease" and "AIDS-related disease" shall refer to any illness or syndrome, caused directly or indirectly by HIV or AIDS-related virus, including but not limited to infections whose source is fungal, viral and/or bacterial.

It is therefore an object of the present invention to employ the CHEs as therapeutic agents in hosts infected with HIV. In vitro studies, ex vivo studies, including the therapeutic indices (TI) calculated for each CHE, suggest that these CHEs will be useful in pharmacological preparations as in vivo anti-HIV agents. The pharmacological preparations may contain the pharmacological active ingredient alone or in admixture with an appropriate excipient or carrier, and administered to the HIV infected host by enteral, such as oral or rectal, and parenteral, such as intraperitoneal, intramuscular, intravenous or subcutaneous route. The pharmacological agent may also be administered in combination with a supplemental antiviral agent, an immune modulator, any other chemotherapeutic agent, an antibody or a combination thereof. In addition, the pharmacological preparations according to the invention may be, for example, in dosage unit form, such as tablets, capsules, suppositories or ampoules.

It is another object of the invention to use a CHE component or combination of CHE components, a biologic metabolite, a derivative thereof or a combination of the above, in a pharmacological preparation for the treatment of HIV-related illness in infected hosts.

It is a further object of the invention to use the CHE, its active component or combination of components, a biological metabolite, a derivative thereof, or a combination of the above, alone or conjugated to a label, in a diagnostic test for the diagnosis of HIV related illness. Such a test could be an immunofluorescent test, based upon a CHE's capacity to bind either the HIV infected T cells or the anti-idiotypic antibody derived from the CHE.

It is still a further object of the invention to use a CHE, a CHE component, a combination of CHE components, a biological metabolite, a derivative thereof, or a combination of the above to produce a vaccine. Once the CHE's "active site" has been determined, current immunologic techniques could be relied upon to produce such a vaccine.

These and other objects will become readily apparent to those skilled in the art from the following description and appended claims.

BRIEF DESCRIPTION OF THE DRAWINGS

The present invention will be described in connection with the accompanying drawings in which.

DETAILED DESCRIPTION

Figure 1:
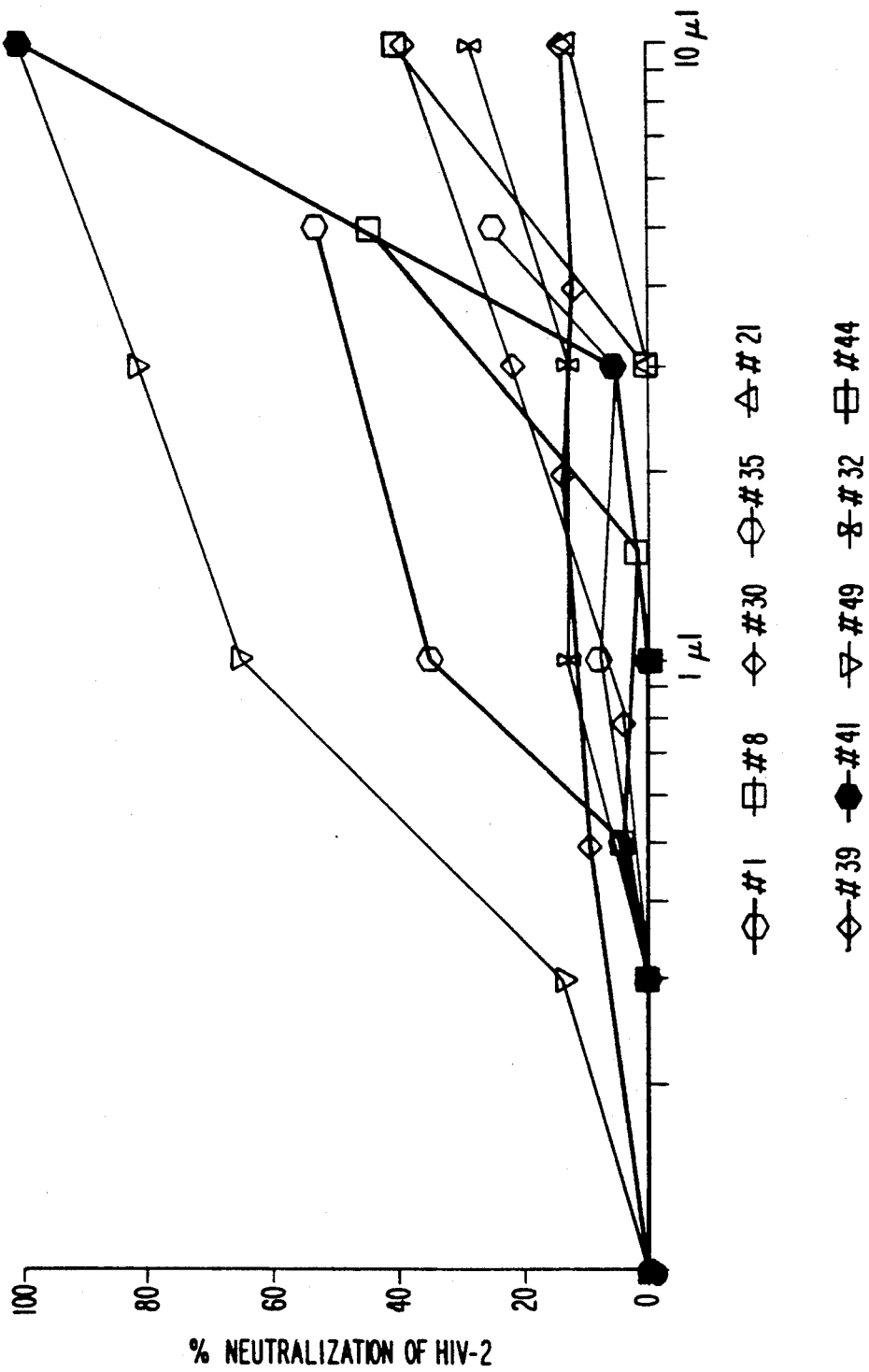
FIG. 1 is a composite graph depicting the neutralization assay results for each of the ten CHEs against the lab isolate IIIB.

The following detailed description and procedures are provided to illustrate the principles of the invention. They are not, however, intended to limit the invention, which extends to the full scope of the appended claims.

A. Preparation of Extracts

The fifty six (56) subject herbs were obtained from China in extract form, packaged in ampoules for parenteral use. However, the extracts of the present invention can be prepared from the subject herbs by utilizing the procedures set forth below, or any organic extraction procedure.

Cut into small pieces, one kilogram of dried herb. Soak the cut herb pieces in eight liters (8 L) of water at room temperature for six to eight hours, and then boil under reflux for one (1) hour. Decant the extract, filter it through a 0.45 $\mu$m membrane filter, and concentrate to one liter (1 L).

To the concentrated extract, add three liters (3 L) of 100% ethanol, and maintain the mixture at room temperature for forty-eight (48) hours. Decant, filter and concentrate the extract to one liter (1 L) as above. Repeat this ethanol precipitation two (2) more times.

Add 0.3% charcoal into the concentrated extract and boil the charcoal-extract mixture for five (5) minutes. Filter the extract again.

To the filtered extract, add 10% sodium hydroxide until pH7. The final extract concentration obtained using these procedures should be 1 g herb/ml.

B. Determination Of The Subtoxic Concentrations Of Herbal Extracts

Before assessing the anti-HIV activity of the fifty-six (56) CHEs, toxicity studies were performed to ensure that the observed activity could not be attributed to the indiscriminate destruction of the host lymphocytes by the CHE. For these studies, the standard laboratory methods for T cell toxicity testing were followed. Chang et al., *Antiviral Research* 9:163-176 (1988); Merchant et al., *Handbook of Cell and Organ Culture*, Burgess Publishing Co., Minneapolis, Minn. (1960).

Briefly, the CHE extract to be tested was diluted two-fold serially in medium. To 0.2 ml of the diluted extract, 0.8 ml of a freshly prepared H9 cell suspension was added. (The H9 cells had been obtained from the American Type Culture Collection (A.T.C.C.).) This was done in duplicate; and a medium control was included in every assay. This medium control consisted of 0.8 ml of the same H9 cell suspension added to 0.2 ml of medium; and the control was done in quadruplicate. After 4 days of incubation, the number of viable cells in each culture was counted with a hemacytometer by dye exclusion. When the viable count of extract-treated culture was 2 S.D. below the mean of the medium control, the extract-treated culture was considered to show evidence of cytotoxicity. The highest concentration of an extract which showed no evidence of cytotoxicity was taken as the subtoxic concentration, or maximum tolerated dose (MTD). The MTD's for the ten (10) CHEs exhibiting anti-HIV activity are disclosed in Table II which follows:

TABLE II

| Maximum Tolerated Dose (MTD) | |
|---|---|
| CHE | MTD ($\mu$l) |
| #1 | 5 |
| #8 | 5 |
| #21 | 40 |
| #30 | 20 |
| #32 | 20 |
| #35 | 10 |

TABLE II-continued

| Maximum Tolerated Dose (MTD) | |
|---|---|
| CHE | MTD ($\mu$l) |
| #39 | 80 |
| #41 | 20 |
| #44 | 40 |
| #49 | 20 |

C. Neutralization Assay

Having determined their MTDs, the fifty-six (56) CHEs were then screened for their inhibitory activity against HIV-IIIB in H9 cells. (The HIV-IIIB had been obtained from Drs. Popovic and Gallo.) Employing a standard neutralization assay, which assay is described in the literature, HIV expression was detected by p24 production in the culture supernatant. Ho et al., *Science* 239:1021-1023 (1988); and Ho et al., *J. Virol.* 61:2024 (1987).

Specifically, the TCID$_{50}$ (50% tissue culture infective doses) for the HIV-IIIB isolate was placed in contact with $1 \times 10^6$ human T lymphocytes, one hour after the CHE under investigation was added at varying doses. This culture was then followed for seven days and observed for signs of viral expression, as measured by the production of HIV core protein p24. A particular CHE was not deemed to have anti-HIV activity unless 90% of viral replication was blocked, as compared to control cultures.

An ID$_{50}$ and ID$_{90}$ (amount of CHE necessary to inhibit 50% and 90% of viral replication, respectively) was also calculated for each of the ten CHEs that exhibited anti-HIV activity. In addition, by dividing the MTD by the ID$_{50}$, a therapeutic index was obtained. Generally, the therapeutic index (T.I.) is a measure of both drug efficacy and safety, and a high therapeutic index is desirable.

FIG. 1 demonstrates the anti-HIV activity of each of the ten (10) CHEs against the lab isolate IIIB. In brief, the ID$_{50}$ for the ten (10) subject CHEs ranged from 0.15 $\mu$l to 1.80 $\mu$l, while the ID$_{90}$ ranged from 0.38 $\mu$l to 2.70 $\mu$l. The T.I. for these same ten (10) ranged from 22 to 173. These values are all presented in Table III below.

TABLE III

| Ten CHEs With Positive Activity Against HTLV-IIIB Infection Of H9 Cells | | | | |
|---|---|---|---|---|
| | | Anti-HTLV-IIIB Activity | | |
| CHE | MTD ($\mu$l) | ID$_{50}$ ($\mu$l) | ID$_{90}$ ($\mu$l) | T.I. |
| #1 | 05 | 0.15 | 0.84 | 33.33 |
| #8 | 05 | 0.14 | 0.38 | 35.71 |
| #21 | 40 | 1.80 | 2.30 | 22.22 |
| #30 | 20 | 0.26 | 1.70 | 76.92 |
| #32 | 20 | 0.45 | 0.66 | 44.44 |
| #35 | 10 | 0.41 | 1.70 | 24.39 |
| #39 | 80 | 1.00 | 5.60 | 80.00 |
| #41 | 20 | 0.34 | 2.70 | 58.82 |
| #44 | 40 | 0.23 | 0.65 | 173.91 |
| #49 | 20 | 0.24 | 0.53 | 83.33 |

Figure 2:
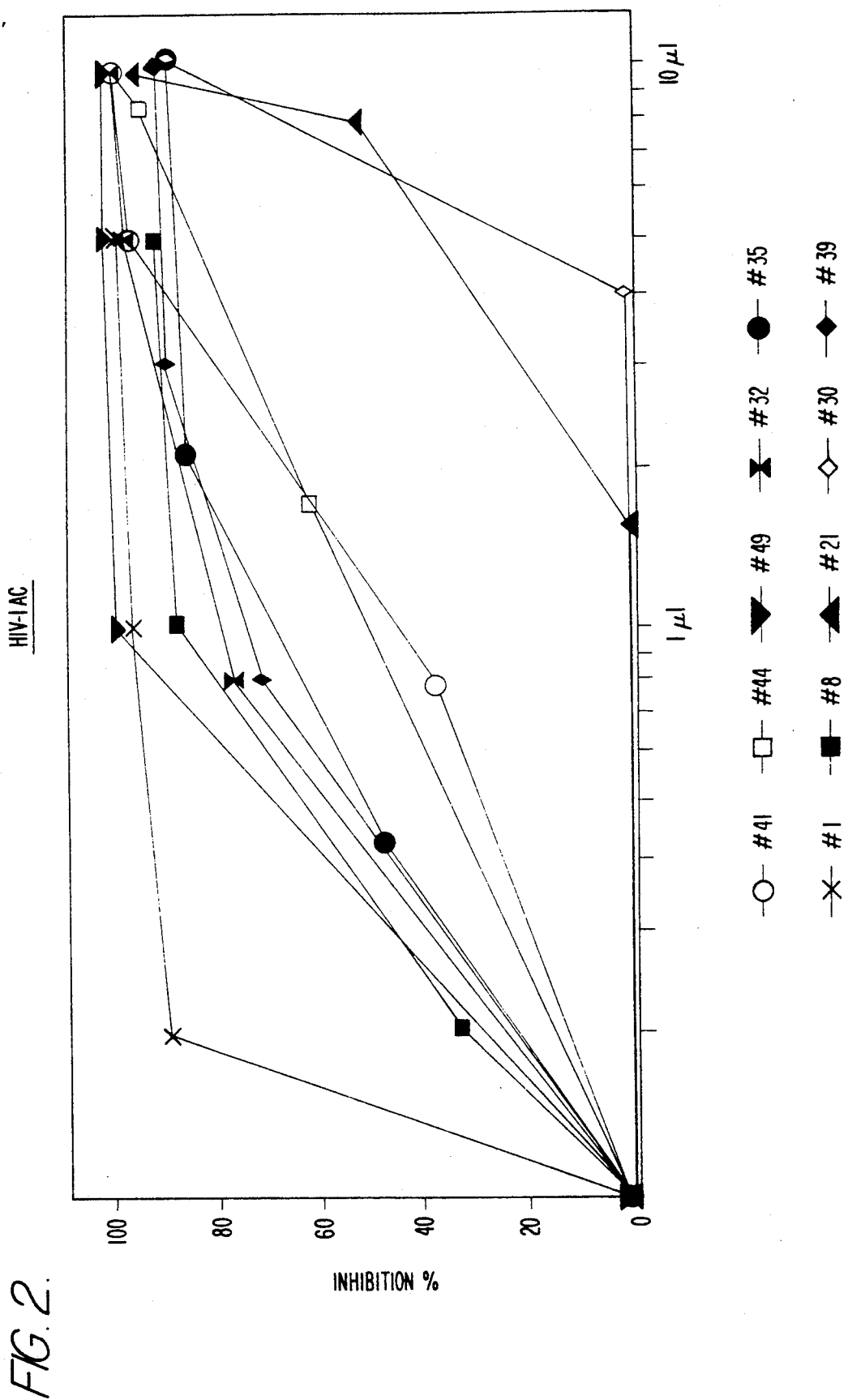
FIG. 2 is a composite graph depicting the activity of the ten (10) CHEs against the laboratory isolate, HIV-1 AC.
Figure 3:
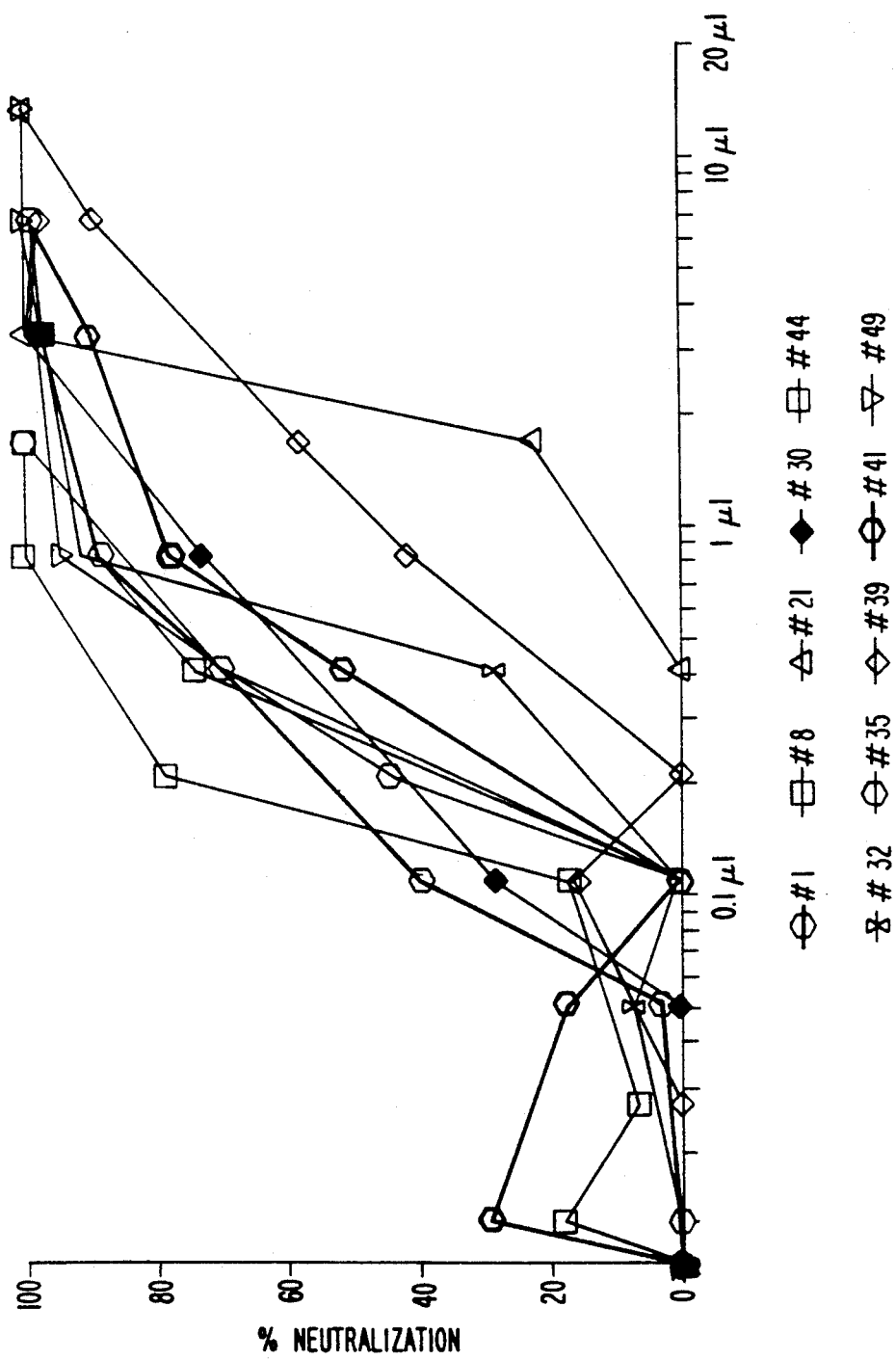
FIG. 3 is a composite graph depicting the neutralization assay results for each of the ten CHEs against the lab isolate HIV-2.
Figure 4:
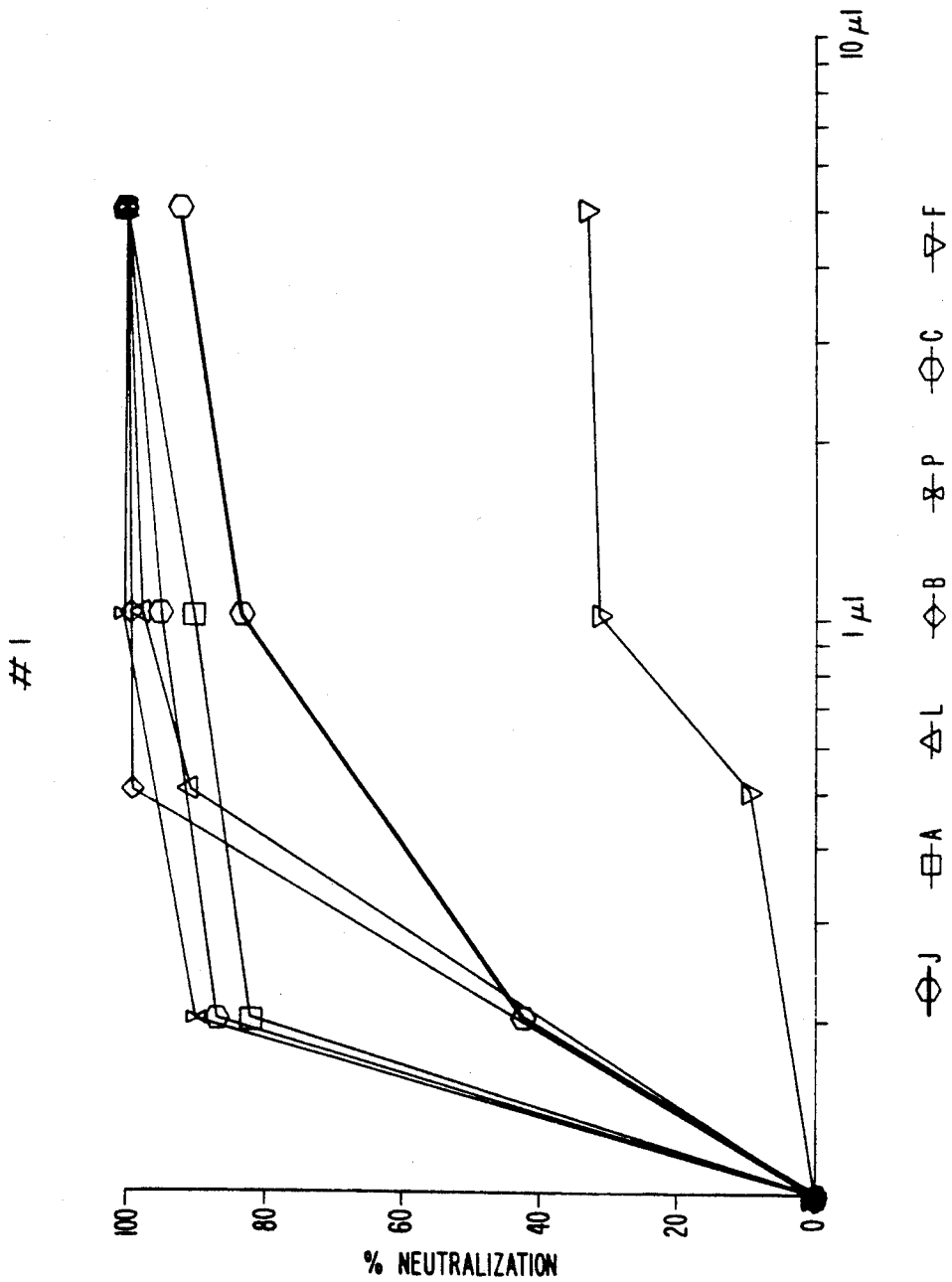
FIG. 4 illustrates and compares the percent HIV neutralization of CHE #1 for each of seven separate clinical isolates of the virus.

Using a similar method, the CHEs were then tested against seven (7) clinical isolates (J, AP, L, B, P, C, F) and two (2) additional HIV laboratory isolates, (AC and HIV2), in normal stimulated PBMNs. (The clinical isolates, and the AC laboratory isolate, had been obtained from AIDS patients treated at Cedars-Sinai Medical Center, in Los Angeles, Calif. The HIV-2 (LAV-2ROD) had been obtained from Luc Montagnier, at the Institute Pasteur, in France.) The ten (10) CHEs were found to exhibit anti-HIV activity against most of the clinical isolates; but with varying efficacy. Similarly, in FIG. 2, all ten (10) CHEs exhibited activity against the AC laboratory isolates, whereas only two (2) of the ten (10) CHEs (#41 and #49), in FIG. 3, showed appreciable inhibitory activity against the HIV2 isolate. The results of this method are discussed more particularly as follows:

As illustrated in FIG. 4, CHE #1 exhibited greater than 90% inhibition for six (6) of the seven (7) primary HIV-1 isolates, with an ID$_{90}$ ranging from 0.20 $\mu$l to 3.5 $\mu$l.

Figure 5:
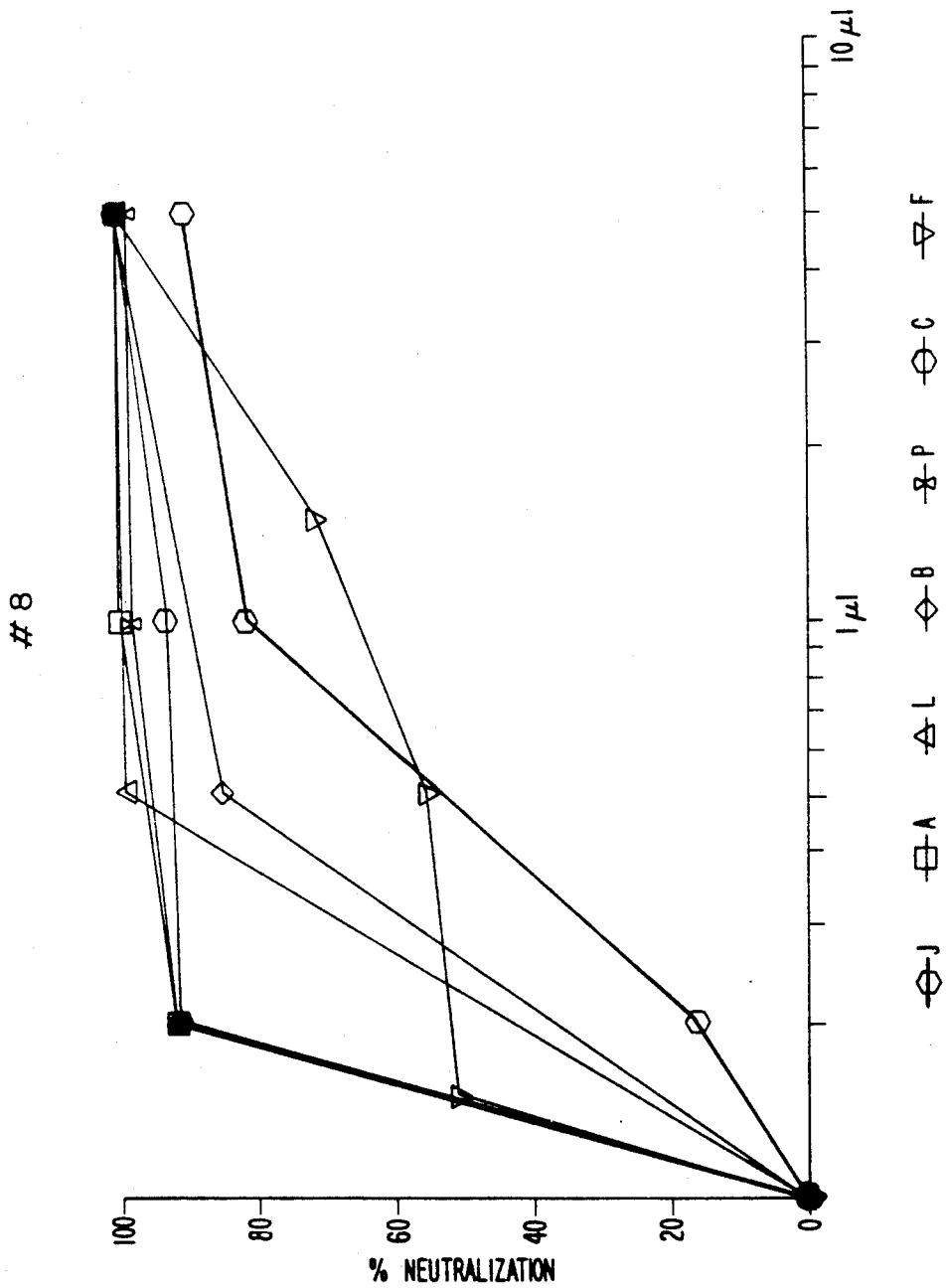
FIG. 5 illustrates and compares the percent HIV neutralization of CHE #8 for each of seven separate clinical isolates of the virus.

In FIG. 5, CHE #8 was found to have equal or greater than 90% inhibition for the seven (7) primary isolates, with an ID$_{90}$ ranging between 0.35 $\mu$l to 5.00 $\mu$l.

Figure 6:
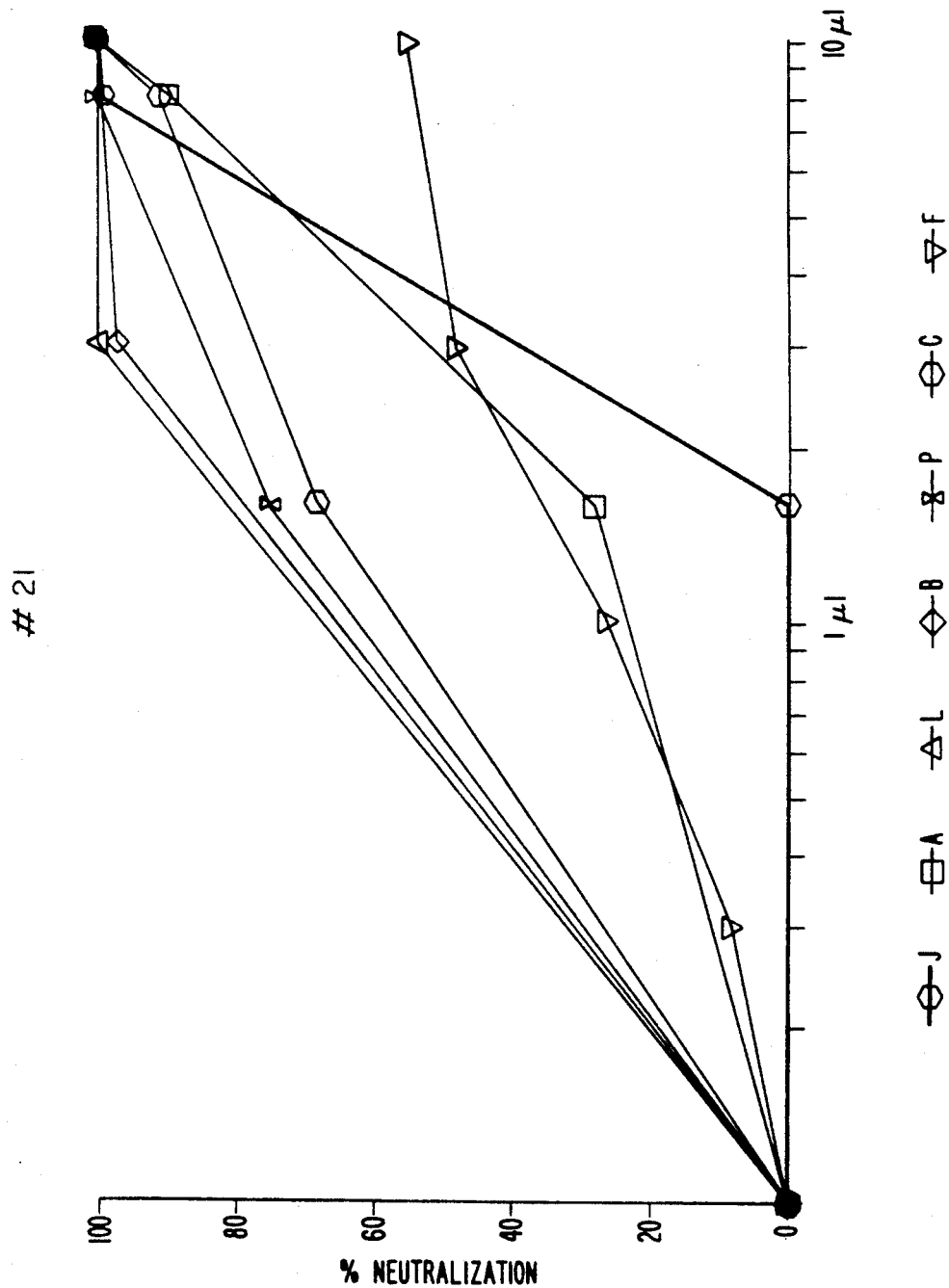
FIG. 6 illustrates and compares the percent HIV neutralization of CHE #21 for each of seven separate clinical isolates of the virus.

As illustrated in FIG. 6, CHE #21 exhibited greater than 90% inhibition for all but one (1) of the seven (7) primary isolates, with an ID$_{90}$ ranging from 1.74 $\mu$l to 7.6 $\mu$l.

Figure 7:
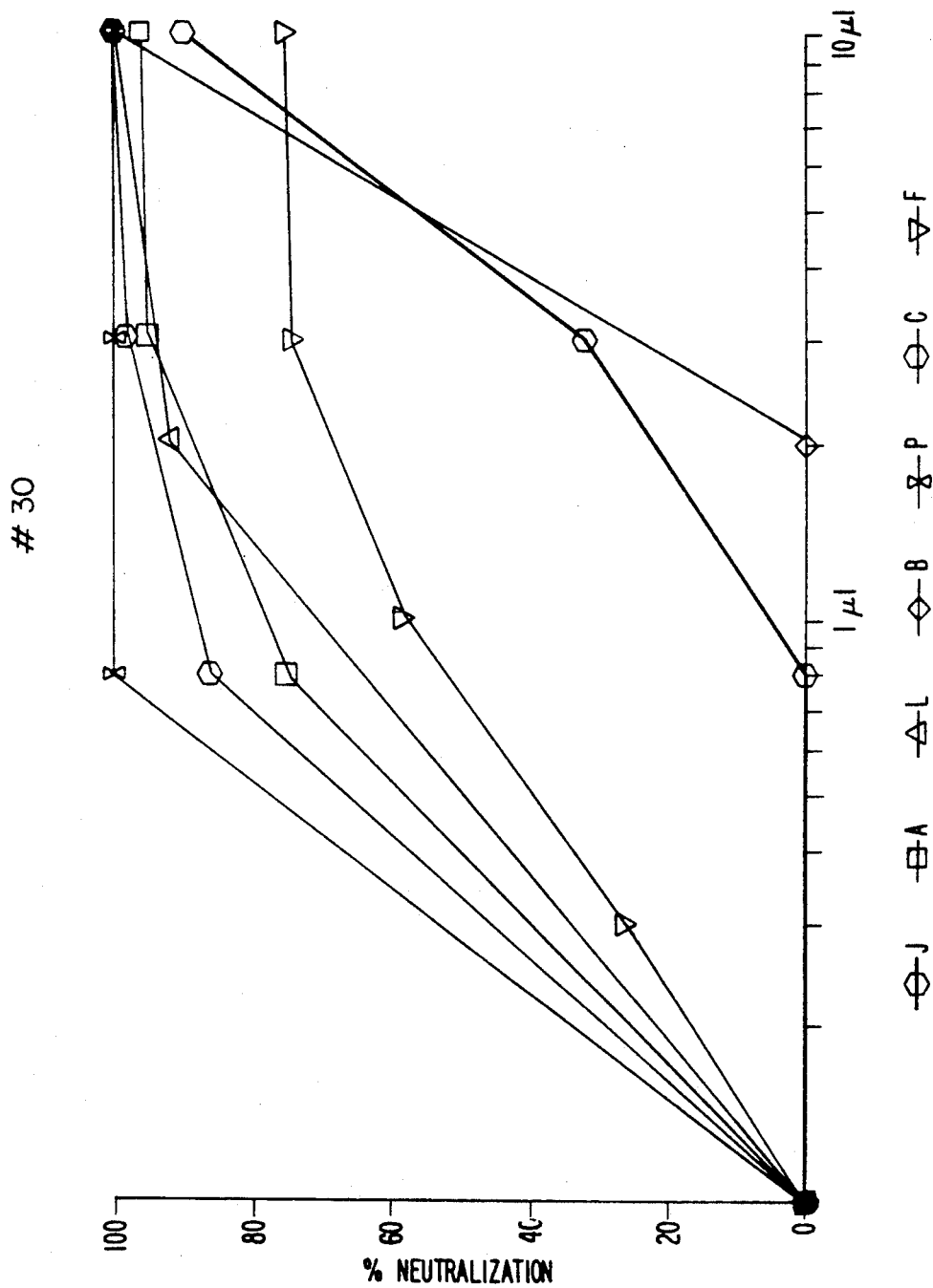
FIG. 7 illustrates and compares the percent HIV neutralization of CHE #30 for each of seven separate clinical isolates of the virus.

In FIG. 7, CHE #30 exhibited greater than 90% activity against five (5) of the seven (7) primary isolates, with an ID$_{90}$ of 0.52 $\mu$l to 8.30 $\mu$l.

Figure 8:
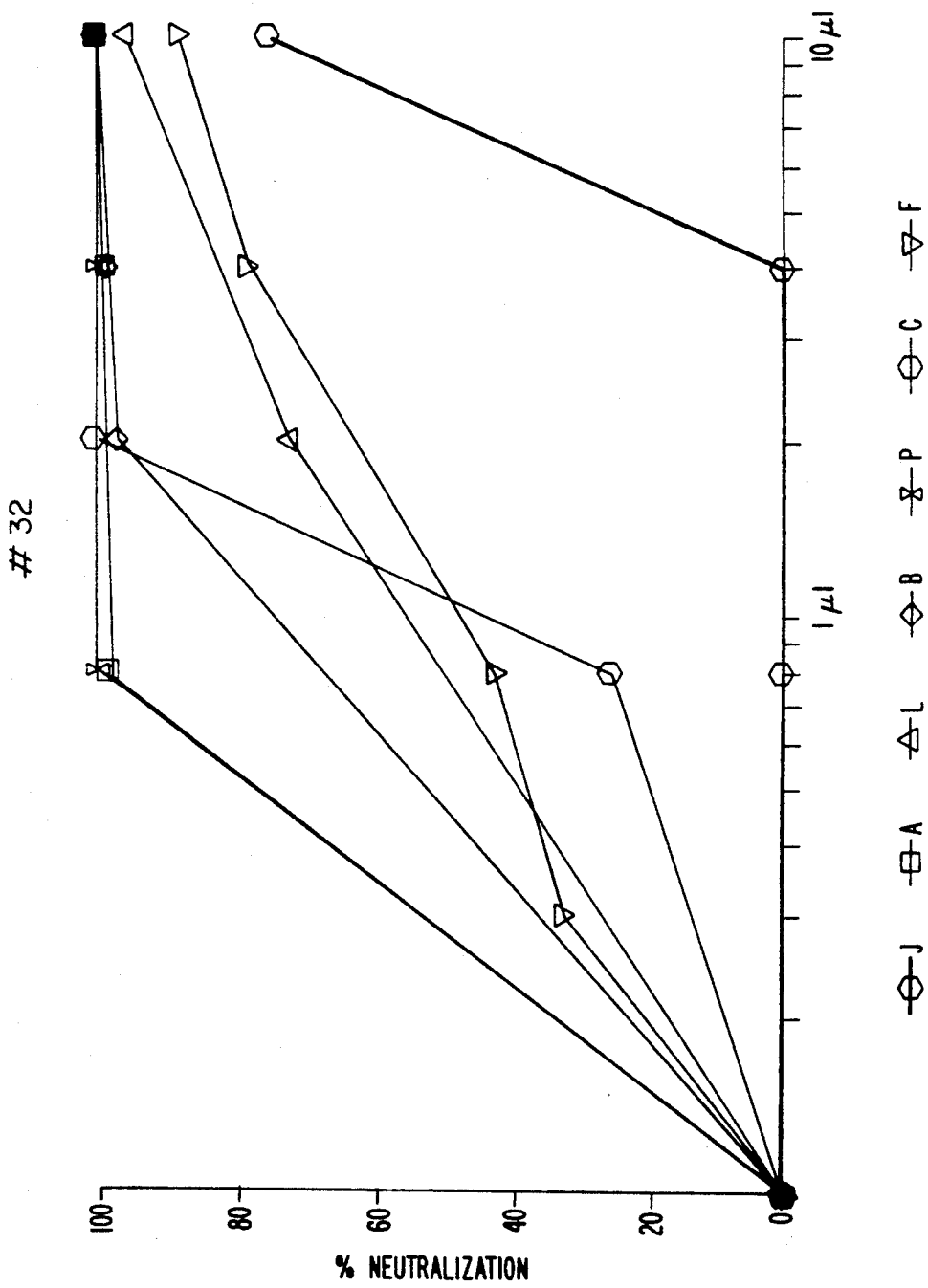
FIG. 8 illustrates and compares the percent HIV neutralization of CHE #32 for each of seven separate clinical isolates of the virus.

FIG. 8 illustrates the neutralization activity for CHE #32. As the graph illustrates, CHE #32 exhibited ID$_{90}$ activity against five (5) of the seven (7) primary isolates, with an ID$_{90}$ ranging from 0.52 $\mu$l to 7.00 $\mu$l.

Figure 9:
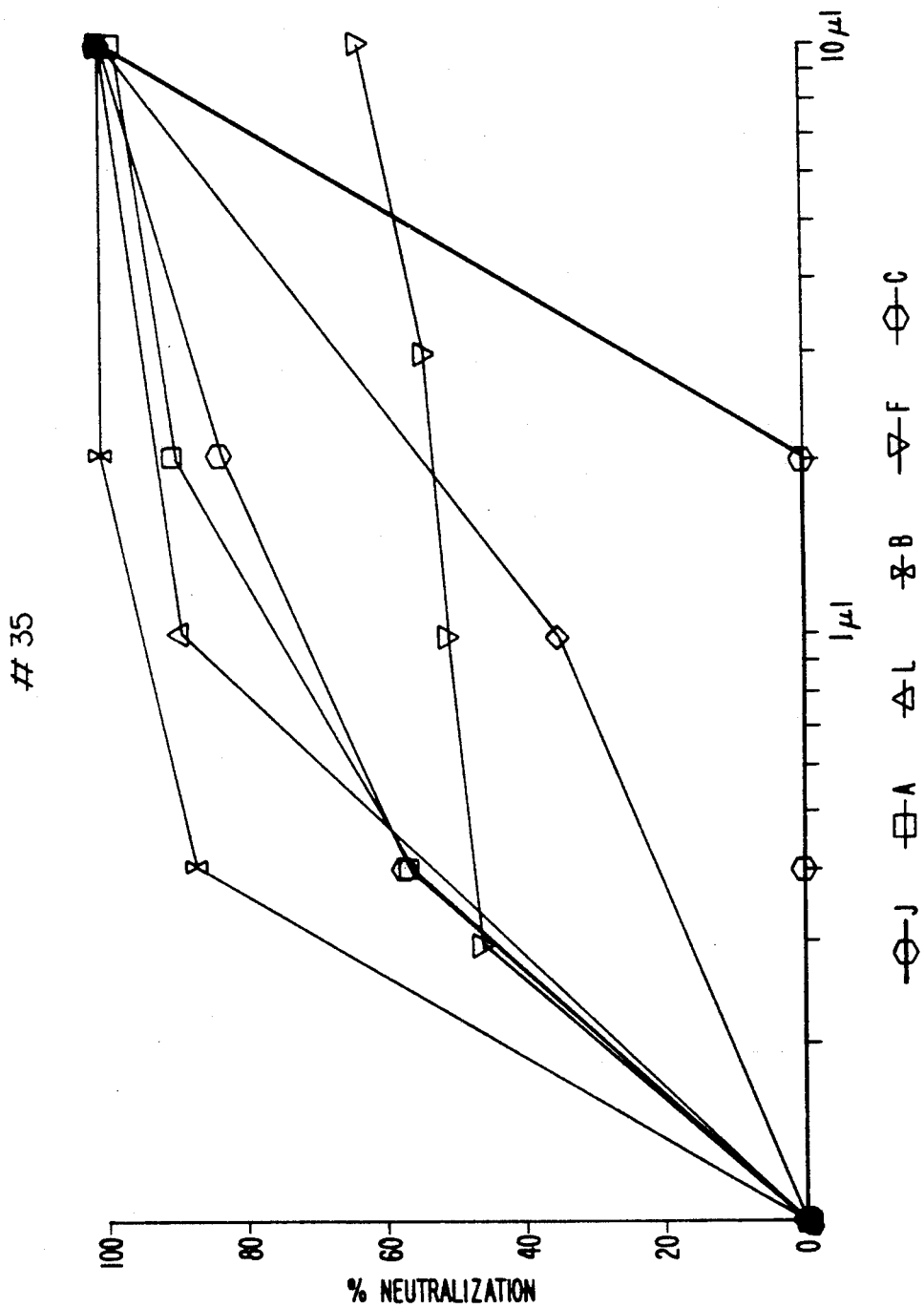
FIG. 9 illustrates and compares the percent HIV neutralization of CHE #35 for each of seven separate clinical isolates of the virus.

In FIG. 9, CHE #35 inhibited six (6) of the seven (7) primary isolates, with an ID$_{90}$ ranging from 0.60 $\mu$l to 8.2 $\mu$l.

Figure 10:
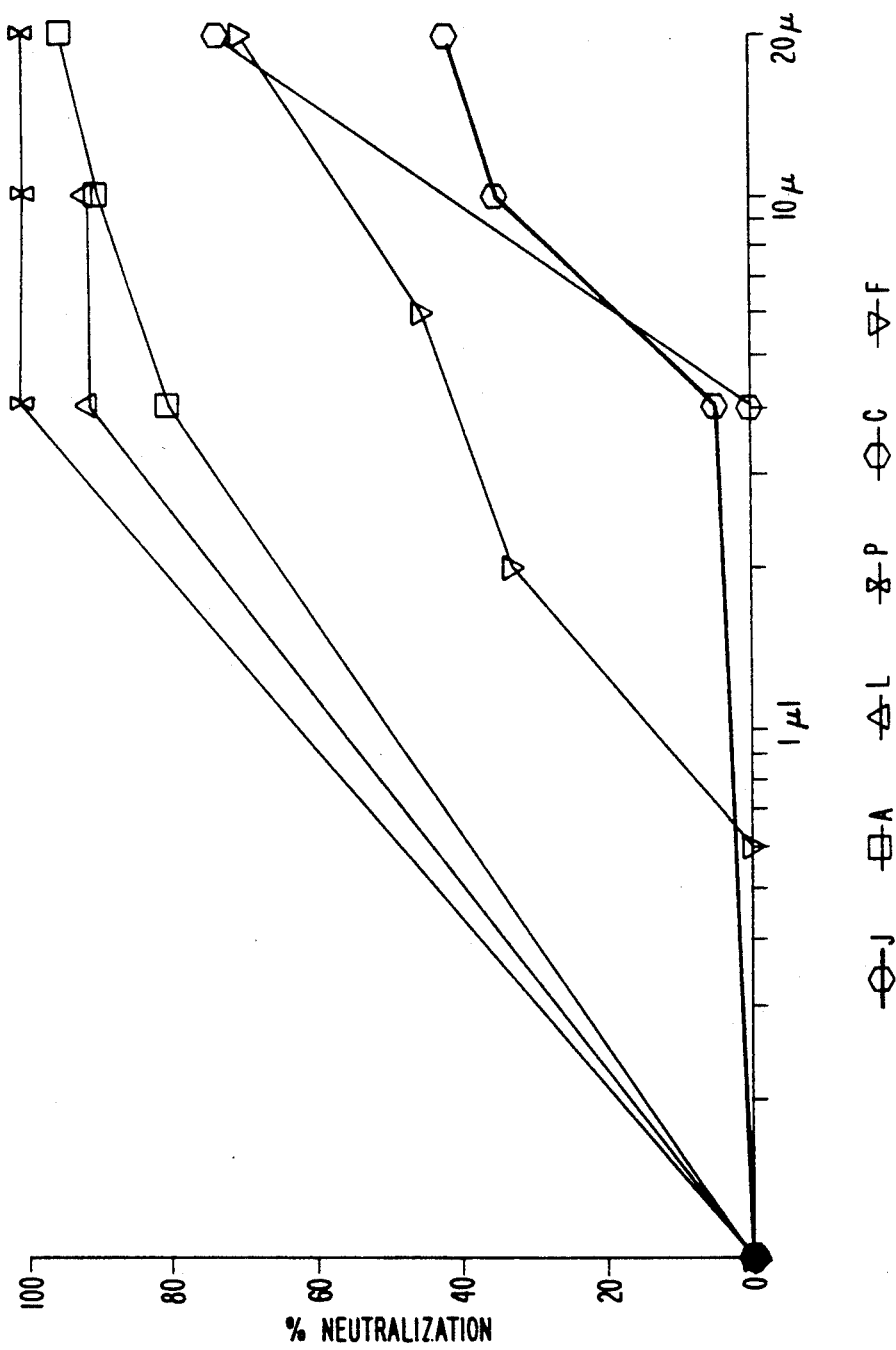
FIG. 10 illustrates and compares the percent HIV neutralization of CHE #39 for each of seven separate clinical isolates of the virus.

As illustrated in FIG. 10, only three (3) of the six (6) primary isolates were inhibited more than 90% by CHE #39, with an ID$_{90}$ ranging from 2.2 $\mu$l to 10 $\mu$l.

Figure 11:
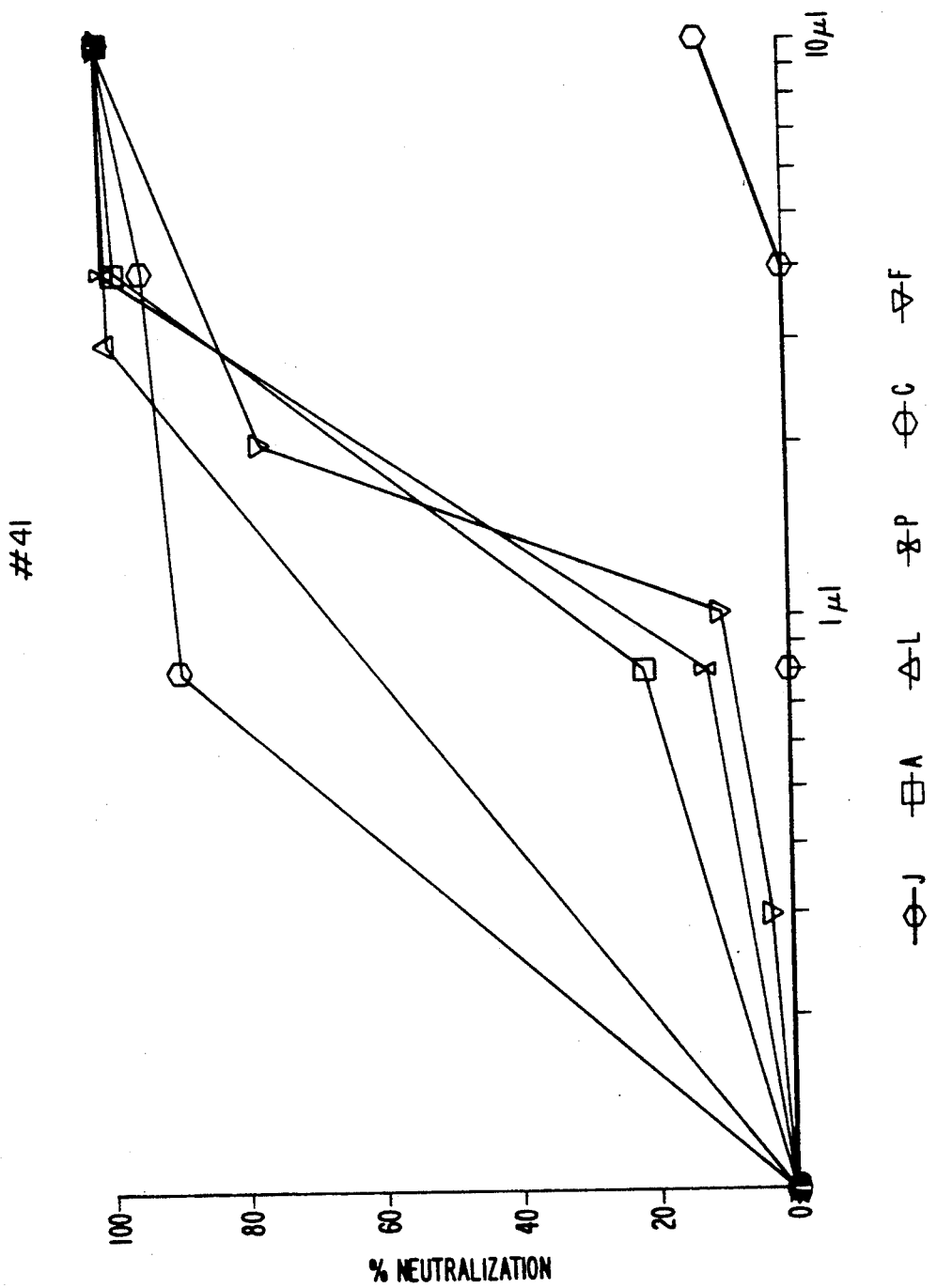
FIG. 11 illustrates and compares the percent HIV neutralization of CHE #41 for each of seven separate clinical isolates of the virus.

In FIG. 11, all but one (1) primary isolate were inhibited greater than 90% by CHE #41, with an ID$_{90}$ between 1.10 $\mu$l to 5.00 $\mu$l.

Figure 12:
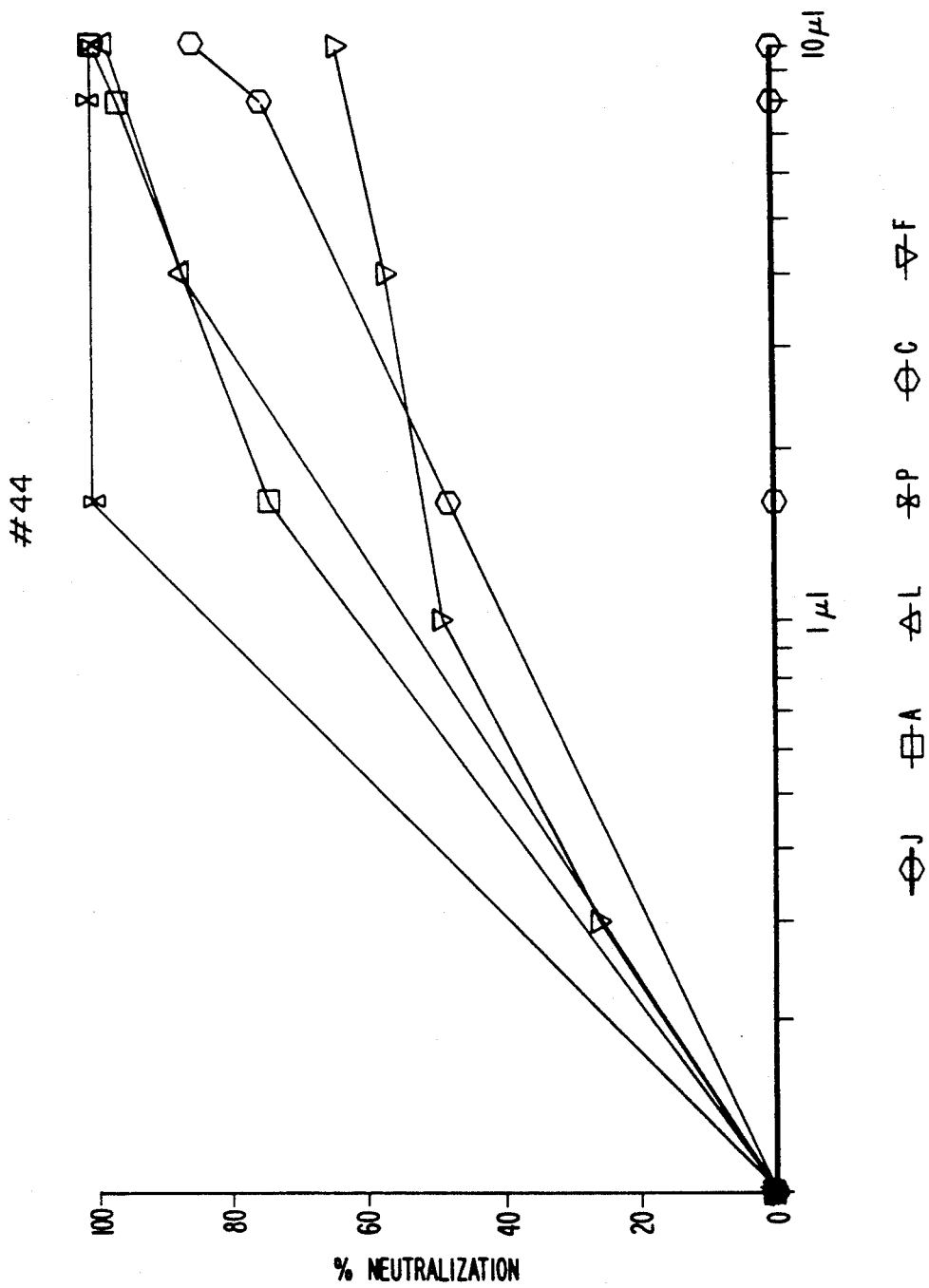
FIG. 12 illustrates and compares the percent HIV neutralization of CHE #44 for each of seven separate clinical isolates of the virus.

CHE #44 exhibited greater than 90% inhibition against three (3) of the six (6) primary isolates in FIG. 12, with an ID$_{90}$ ranging from 1.00 $\mu$l to 5.10 $\mu$l.

Figure 13:
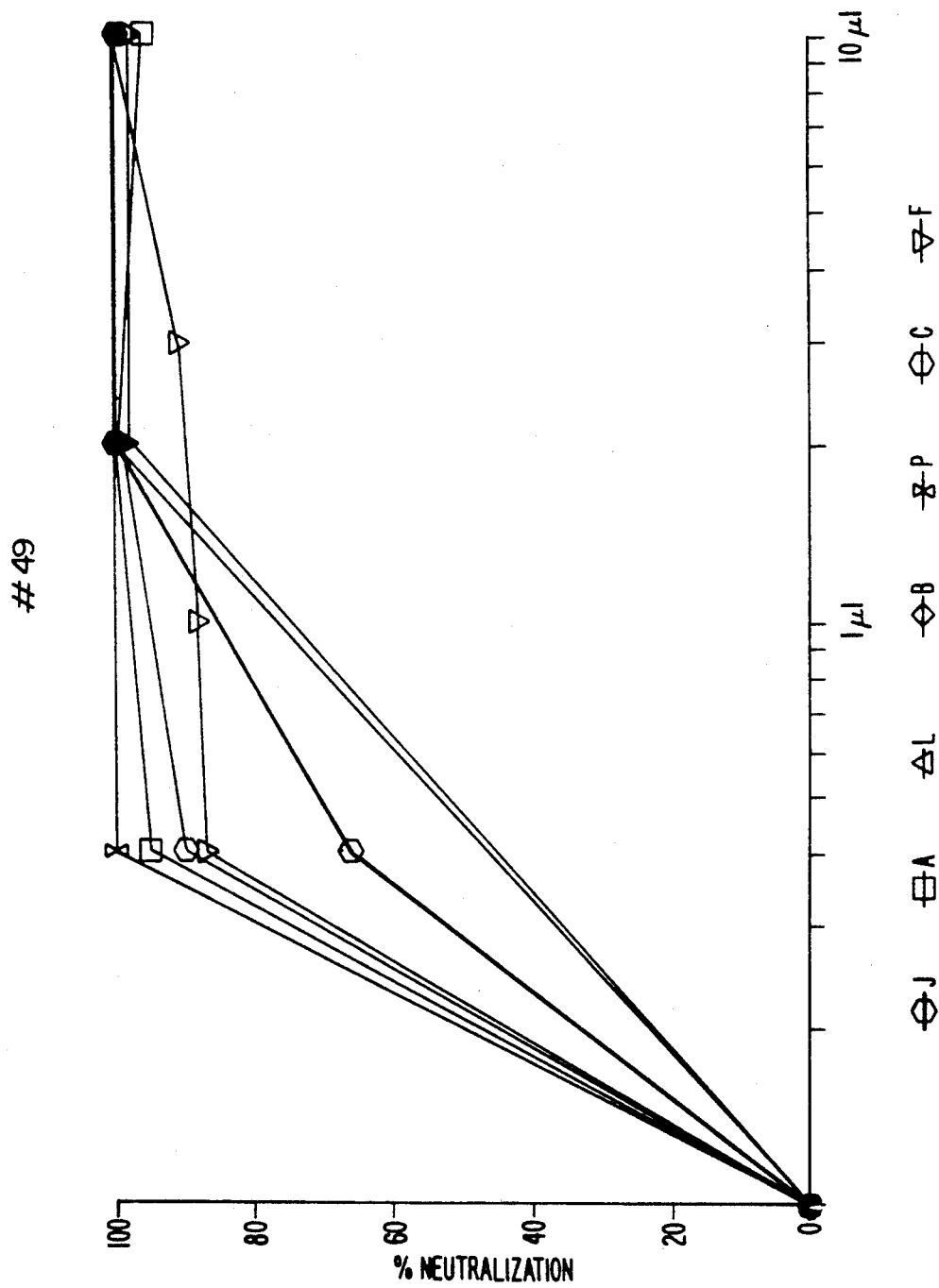
FIG. 13 illustrates and compares the percent HIV neutralization of CHE #49 for each of seven separate clinical isolates of the virus.

In FIG. 13, CHE #49 inhibited all seven (7) primary isolates by greater than 90%, with an ID$_{90}$ of 0.62 $\mu$l to 2.05 $\mu$l.

D. Syncytial Inhibition

Formation of syncytia, with progression to cell death, is a characteristic feature of in vitro cell cultures infected with HIV. Syncytia formation depends upon the interaction of HIV-expressing cells with neighboring cells bearing the CD4 differentiation antigen. Syncytial inhibition studies were therefore performed to determine whether a particular CHE had its primary effect upon the HIV envelope glycoproteins, or upon the uninfected target cells. Following a standard method, described in the literature, the two cell cultures Molt IIIB and HPBALL were employed as the sources of infected and uninfected cell specimens, respectively. See Lifson et al., *Science* 232:1123-7 (1986); Sodroski et al., *Nature* 322:470-4 (1986); and Lifson et al., *Nature* 323:725-8 (1986).

Varying amounts (0.3 $\mu$l, 1.0 $\mu$l, 3.0 $\mu$l) of each of the ten (10) CHEs were preincubated separately with either the infected Molt IIIB or the uninfected HPBALL cells for a standard time period. The cells were then washed several times and the two cell types were mixed in culture. The percent syncytial inhibition of both methods was then evaluated for all CHEs by light microscopy eighteen (18) hours after mixing. Table IV lists the preliminary results of syncytial inhibition activity exhibited by each CHE studied.

TABLE IV*

|  | #1 | #8 | #21 | #30 | #32 | #35 | #39 | #41 | #44 | #49 | rsT4 |
|---|---|---|---|---|---|---|---|---|---|---|---|
| A. CHE WAS PREINCUBATED WITH UNINFECTED CELLS (HPB-ALL) |||||||||||||
| 3 μl | 96.2 | 98.1 | 3.7 | 70.9 | 93.6 | 98.1 | 67.9 | 77.4 | 50.9 | 86.1 | 32.1 (3 μl) |
| 1 μl | 62.3 | 26.4 | 1.9 | 62.3 | 74.7 | 83.0 | 15.1 | 58.5 | 35.8 | 62.3 | 35.8 (1 μl) |
| 0.3 μl | 28.3 | 15.1 | 0 | 28.3 | 37.7 | 58.5 | 0 | 16.9 | 15.5 | 50.9 | 0 (0.3 μl) |
| B. CHE WAS PREINCUBATED WITH INFECTED CELLS (MoltIIIB) |||||||||||||
| 3 μl | 0 | 20.8 | 7.6 | 47.2 | 73.6 | 26.4 | 39.6 | 50.6 | 92.5 | 73.6 | 92.5 (3 μl) |
| 1 μl | 0 | 26.4 | 13.2 | 39.6 | 37.2 | 20.8 | 16.9 | 50.9 | 88.7 | 47.2 | 62.3 (1 μl) |
| 0.3 μl | 0 | 9.4 | 0 | 16.9 | 33.9 | 0 | 18.3 | 43.4 | 77.4 | 32.1 | 35.8 (0.3 μl) |

*The results tabulated above were obtained from one (1) series of experiments. These experiments have not yet been repeated to verify the reproducability of the above results.

Briefly, as tabulated above in Section A of Table IV, four (4) of the ten (10) CHEs (#1, #8, #32 and #35) exhibited greater than 90% inhibition of syncytia formation when the CHE was preincubated with the uninfected cells. However, only one (1) (#44) exhibited greater than 90% inhibition of syncytia formation when the CHE was preincubated with the infected cells.

Figure 14:
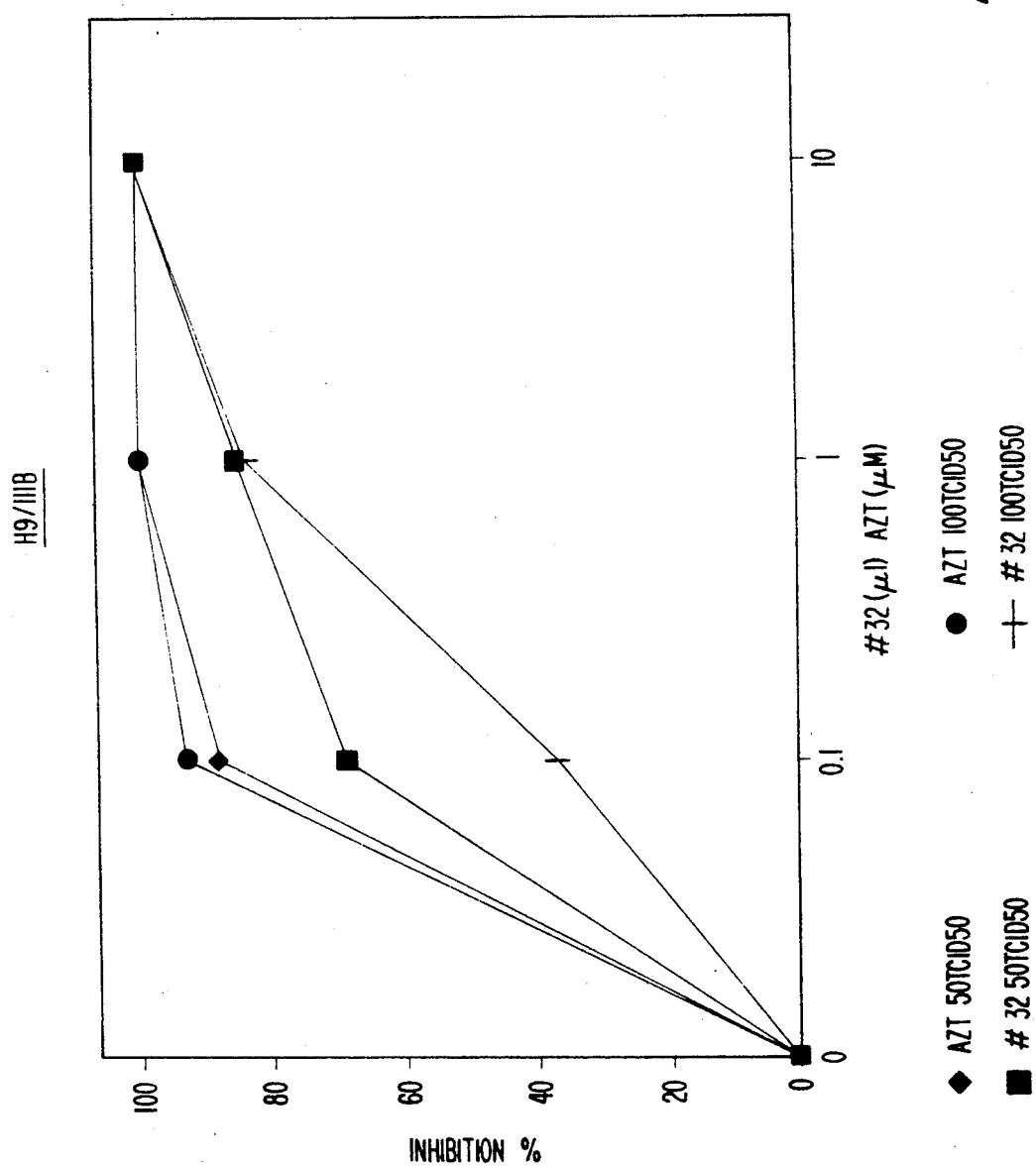
FIG. 14 is a composite graph depicting the degree of HIV replication inhibition exhibited by CHE #32.

An additional experiment was thereafter performed to determine whether this anti-HIV activity produced by the CHEs occurred inside the cells. In this experiment, the cells were infected one (1) hour before adding the CHEs, using the reverse transcriptase inhibitor, AZT, as a control. In FIG. 14, 10 μl of CHE #32 exhibited 100% inhibition of HIV replication in the preinfected cells with both doses of HTLV-IIIB (50 TCID$_{50}$ and 100 TCID$_{50}$). This result appears to indicate that the observed in vitro anti-HIV activity may actually occur within the cell, although the precise mechanism for this activity is still being investigated.

E. End-Point-Dilution Cultures

Figure 15:
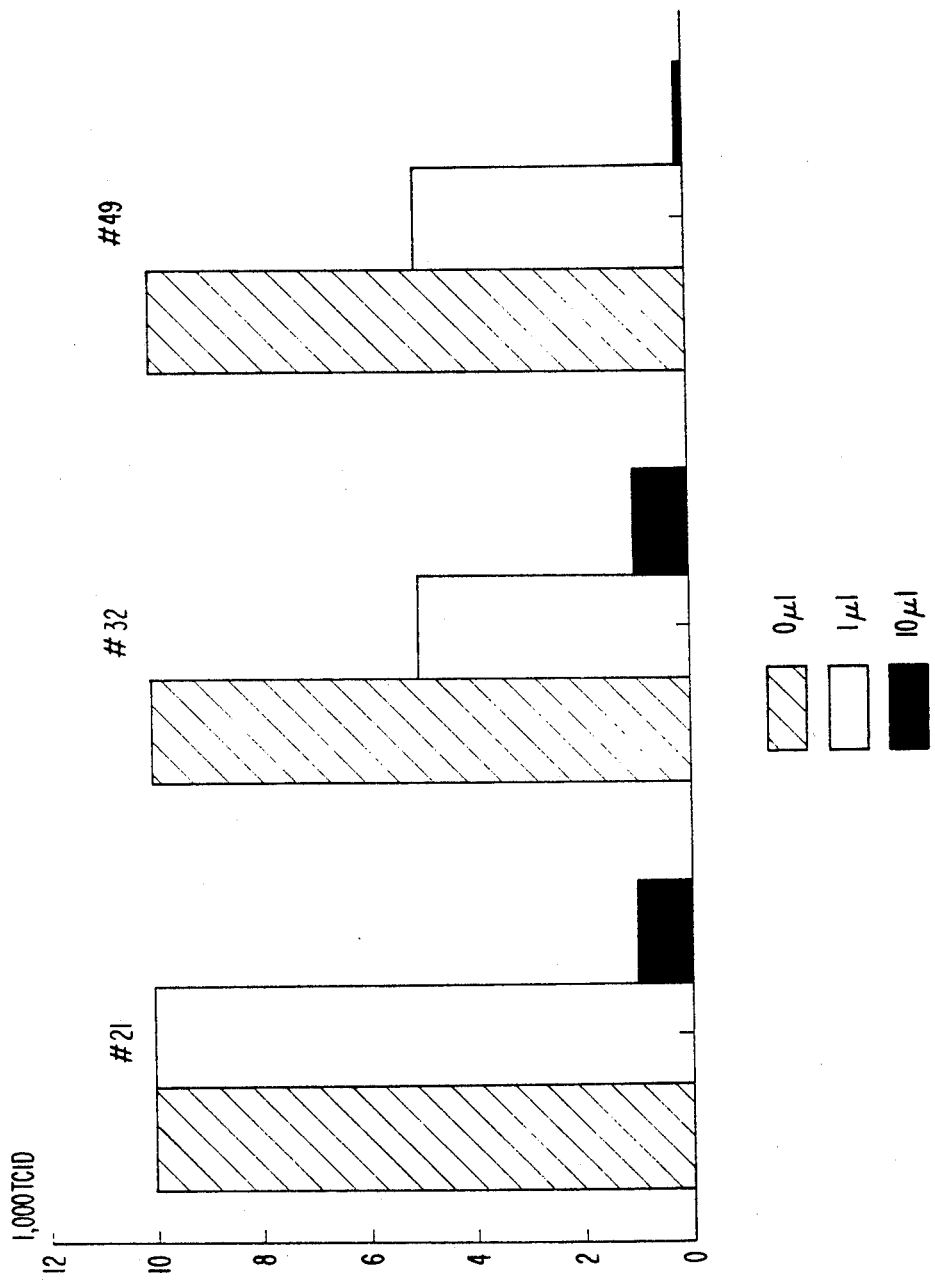
FIG. 15 illustrates and compares the anti-HIV activity of CHEs #21, #32 and #49 in chronically infected H9/IIIB cells.

The end-point-dilution culture method, as described in the literature, was used to determine whether the CHEs exhibited an anti-HIV effect in chronically infected H9/IIIB cells. Ho et al., NEJM 321:1621–1625 (1989). As indicated in FIG. 15, 1 μl of CHE #21 produced no viral titer change, although 10 μl of CHE #21 produced a 10 fold decrease in viral titer. Moreover, 1 μl of CHE #32 produced a 2 fold decrease in viral titer, while 10 μl produced a 10 fold decrease; and 1 μl of CHE #49 decreased the viral titer 2 fold, while 10 μl resulted in a 100 fold decrease.

Hence, these results further strengthen the results obtained in the pre-infection studies in FIG. 14, (the cells were infected one hour before adding the CHEs), where it appeared that the anti-HIV activity of the CHEs may actually occur within the cell interior. However, as indicated above, the precise mechanism for the CHE activities is still under investigation.

F. Reverse Transcriptase Assay

The HIV III-B RT enzyme was isolated and mixed with varying amounts of each CHE, using a known reverse transcriptase (RT) biochemical assay. Ho et al., Science 226:451–453 (1984); Popovic et al., Proc. Natl. Acad. Sci. U.S.A., 77:7415 (1980).

Specifically, virus particles were precipitated from cell-free supernatant as follows: 0.3 ml of 4M sodium chloride and 3.6 ml of 30% (weight volume) polyethylene glycol (Carbowax 6000) were added to 8 ml of harvested culture fluids and the suspension was placed on ice overnight. The suspension was centrifuged at 2000 rev/min at 30 minutes. The precipitate was resuspended in 300 μl of 50% (by volume) glycerol (25 mM tris-HCl, pH 7.5, 5 mM dithiothreital, 150 mM potassium chloride and 0.025% Triton X-100). Virus particles were disrupted by addition of 100 μl of 0.9% Triton X-100/1.5M potassium chloride solution.

Figure 16:
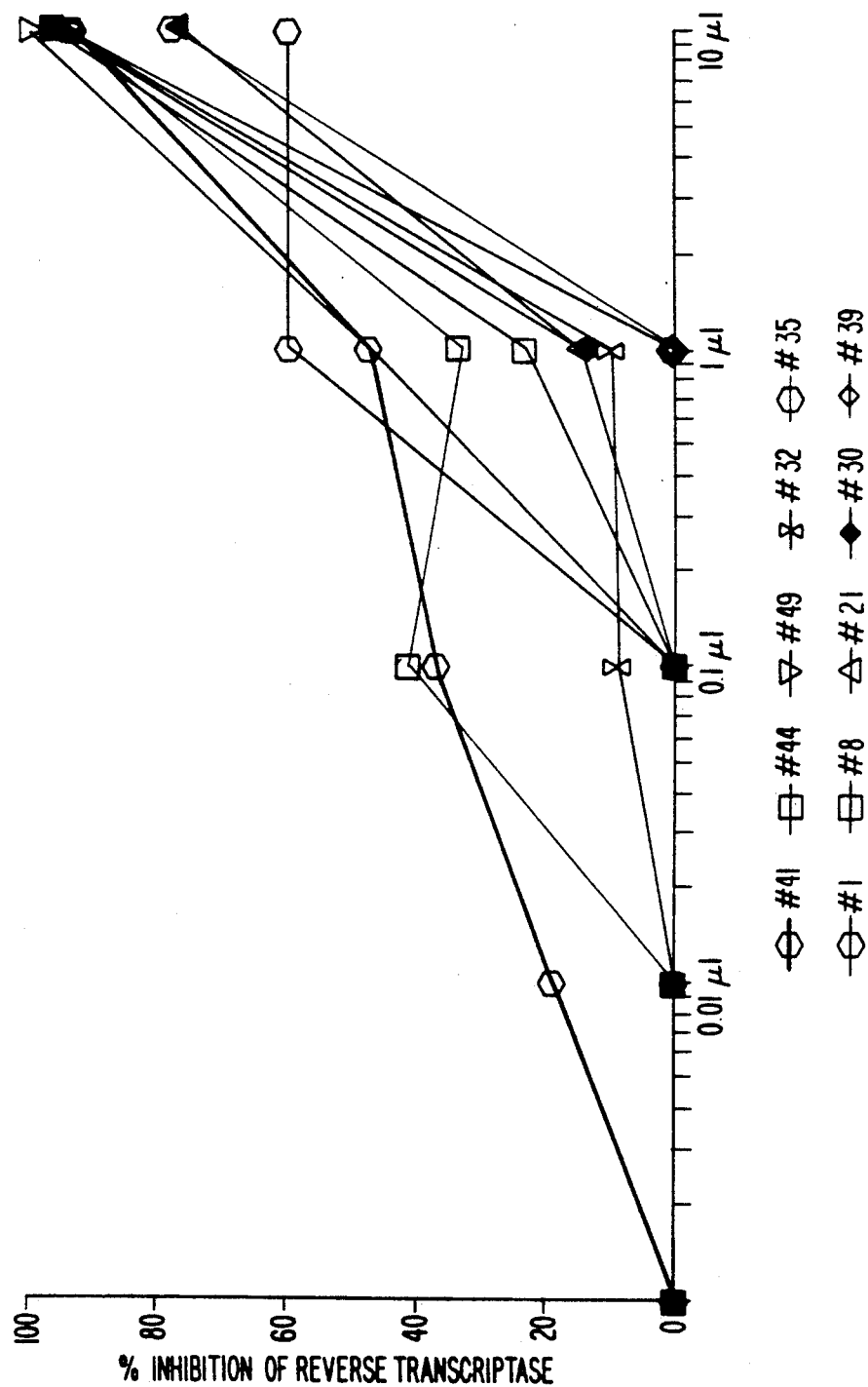
FIG. 16 is a composite graph depicting each CHE's percent neutralization of HIV IIIB reverse transcriptase activity.

The cell-free virus concentrate from a culture of H9/HIV III-B was layered on a 20 to 60% (by weight) sucrose gradient in 10 mM tris-HCl (pH 7.4) containing 0.1M sodium chloride and 1 mM EDTA and centrifuged overnight at 35,000 rev/min. Fractions of 0.7 ml were collected from the bottom of the gradient and 10 μl portions, in a final volume of 100 μl containing 40 mM tris-HCl (pH 7.8), 4 mM dithiothreital, 45 mM potassium chloride and 50 μg of template—primer poly (A).dT$_{12-18}$ and poly (C).dG$_{12-18}$ per ml (with 10 mM Mg$^{2+}$) or 50 μl of poly (dA).dT$_{12-18}$ per ml (with 0.25 mM Mn$^{2+}$) were assayed for RT at 37° C. for 1 hour. The mixture also contained 15 μM of the appropriate labeled deoxyribonucleotide triphosphates, [$^3$H]dTTP (16 Ci/mmole; 1 Ci-3.7×10$^{10}$ becquerels) or [$^3$H]dGTP (12 Ci/mmole). The amount of each CHE necessary to inhibit 50% and 90% of the HIV III-B RT activity is reported in Table V below and FIG. 16. As illustrated, the results indicate that seven (7) of the ten (10) CHEs exhibited greater than 90% RT inhibition.

TABLE V

| CHE | Anti-HTLV-IIIB RT Activity ||
|---|---|---|
|  | ID$_{50}$ (μl) | ID$_{90}$ (μl) |
| #1 | 0.53 | >10.00 |
| #8 | 2.40 | 9.00 |
| #21 | 3.70 | >10.00 |
| #30 | 1.60 | 9.00 |
| #32 | 3.00 | 9.00 |
| #35 | 4.50 | >10.00 |
| #39 | 3.35 | 8.90 |
| #41 | 1.20 | 9.20 |
| #44 | 1.95 | 9.50 |
| #49 | 1.12 | 6.80 |

G. Ex Vivo Experiments Utilizing CHEs #32 And #49, The Best Mode CHEs

Having determined their in vitro anti-HIV activity, ex vivo experiments were conducted in order to provide an experimental model that resembles as closely as possible, in vivo conditions for the CHEs. Ho et al., PNAS, 87:6574–6578 (1990). For these experiments, CHEs #32 and #49 were utilized, as they were considered the leading candidates among the ten (10) CHEs for anti-HIV activity. These two (2) particular (CHEs) were selected based upon the experimental data to date. However, this selection of CHEs #32 and #49 as the best mode CHEs is not meant to foreclose other possibilities, as future experiments may identify other more effective anti-HIV agents among the ten (10) CHEs.

Figure 17:
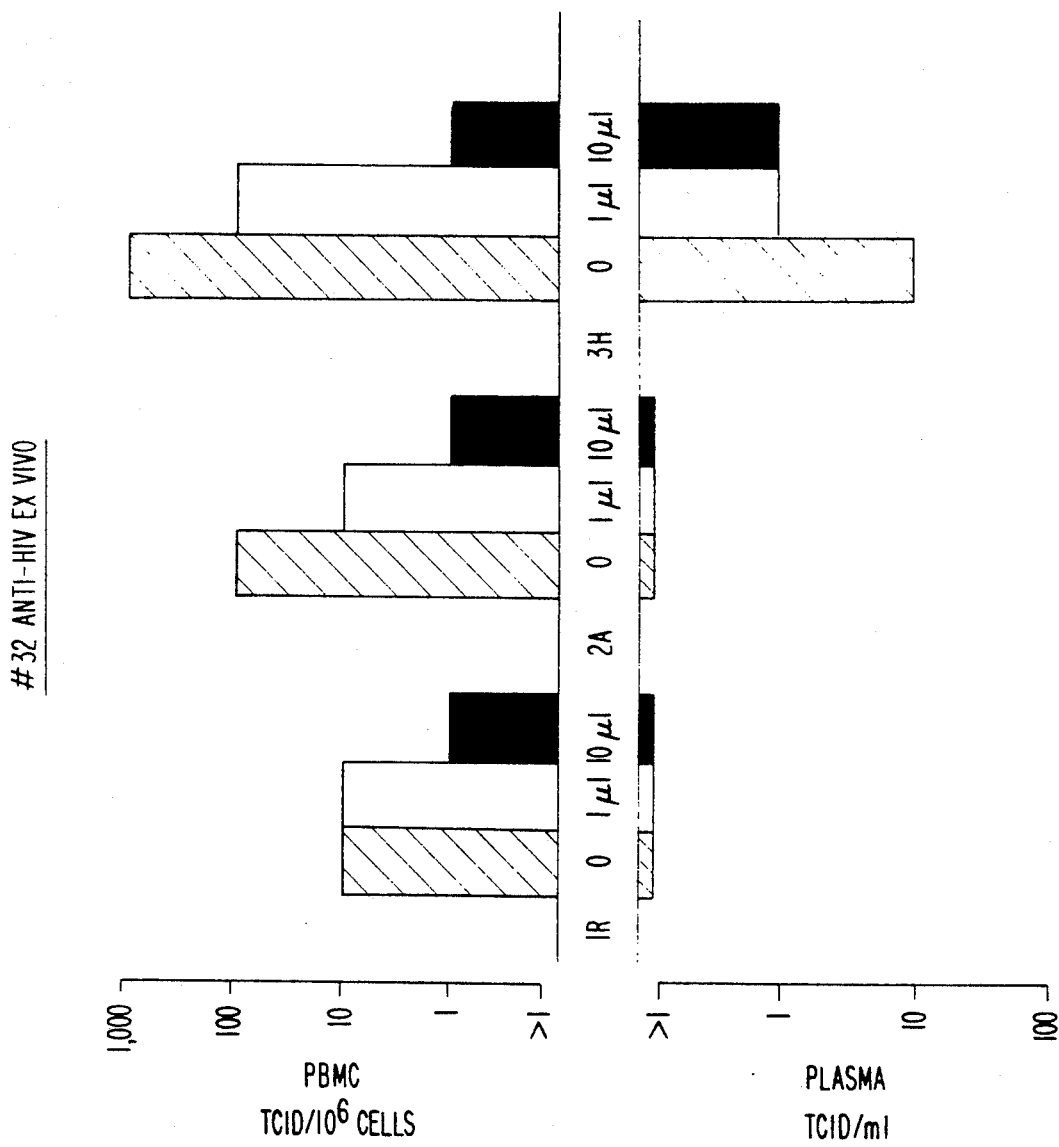
FIG. 17 illustrates and compares the ex vivo anti-HIV activity of CHE #32 in the peripheral blood mononuclear cells (PBMNs) and plasma of three (3) patients.

Plasma and PBMNs were obtained from three (3) patients and denoted as follows: A, for a patient with AIDS; R for a patient with ARC; and H for a healthy patient. An end-point-dilution culture method as described above, was used for serial quantitation of HIV-1 in the PMBNs and plasma of the three (3) patients, and serum p24 core antigen levels were measured as a marker of viral burden. In FIG. 17, the HIV titers in PBMNs are illustrated on the top graph; and the HIV titers in plasma are illustrated on the bottom graph.

HIV-1 was recovered from the PBMNs of all three (3) patients, with titers ranging from 10 to 1,000 TCID/$10^6$ cells, and a mean titer of 370 TCID/$10^6$ cells. When 1 μl of CHE #32 was added, however, HIV-1 was detected in titers ranging from 10 to 100 TCID/$10^6$ cells, a 10 fold decrease in viral titers. When 10 μl of CHE #32 was added, viral titers in all patients were decreased to 1 TCID/$10^6$ cells. Meanwhile, the total HIV-1 titers in plasma before the addition of CHE ranged from less than 1 to 10 TCID/ml, and a mean value of 3.3 TCID/ml. However, the addition of 1 μl or 10 μl of CHE #32 decreased viral titers to less than 1 to 1 TCID/ml.

Figure 18:
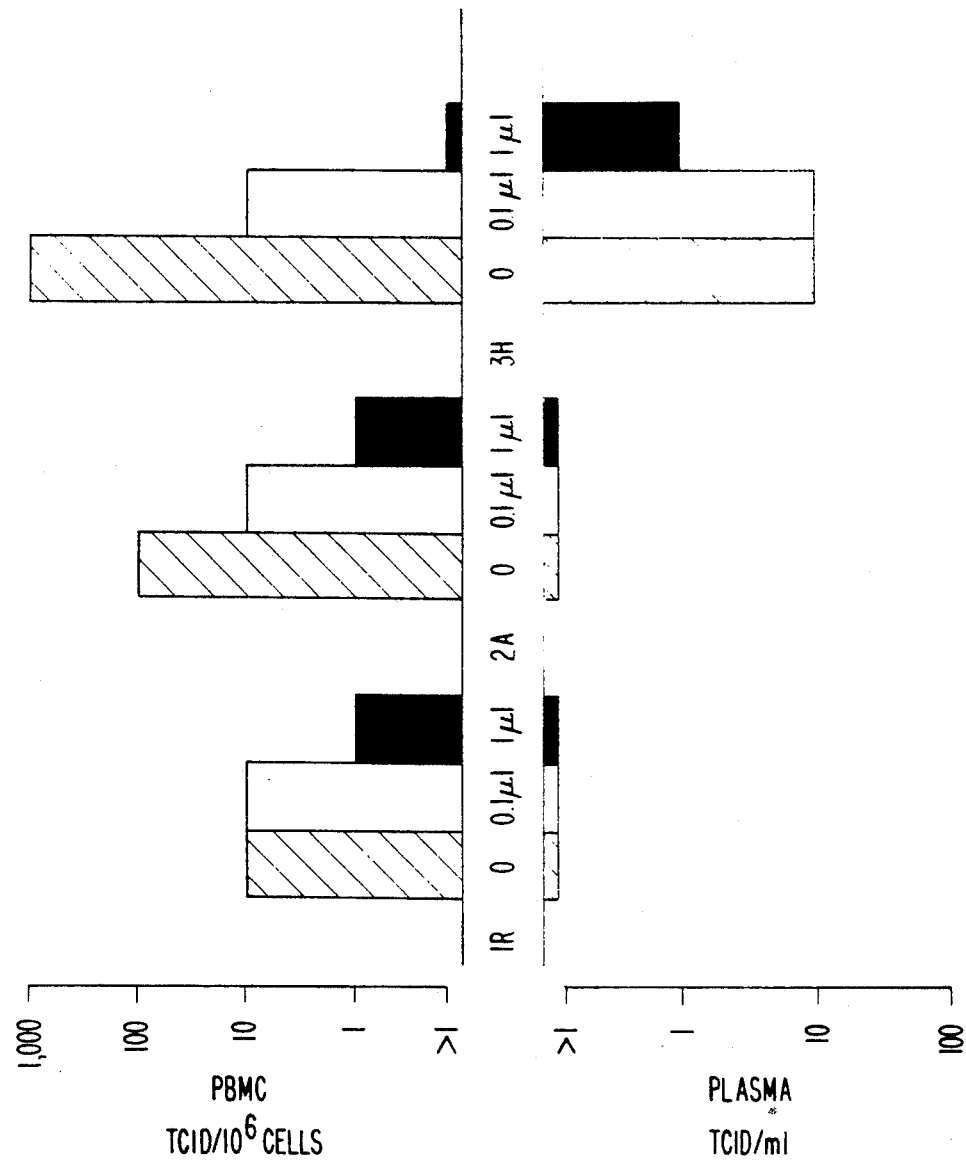
FIG. 18 illustrates and compares the ex vivo anti-HIV activity of CHE #49 in the PBMNs and plasma of three (3) patients.

As illustrated in FIG. 18, in PBMNs treated with 0.1 μl of CHE #49, HIV titers decreased from a mean titer of 370 TCID/$10^6$ to 10 TCID/$10^6$ cells. The addition of 1 μl of CHE #49 further reduced the viral titer to 0.67 TCID/$10^6$ cells. In plasma, however, 0.1 μl of CHE #49 produced no change in HIV titer, although 1 μl reduced the HIV titer 10 fold.

These experiments and the resulting data demonstrate that CHEs may be a rich source for potential in vivo anti-HIV therapy in an infected host. As illustrated, ten (10) of the fifty-six (56) CHEs tested were found to exhibit dose dependent anti-HIV activity in vitro. Five (5) of these CHEs (#1, #8, #32, #35 and #44) also demonstrated substantial syncytial inhibition activity, while seven (7) CHEs (#8, #30, #32, #39, #41, #44 and #49) exhibited inhibitory activity against reverse transcriptase. Finally, CHEs #32 and #49 even exhibited ex vivo dose dependent anti-HIV activity in patient plasma and PBMNs.

We claim:

1. A method of inhibiting in vitro HIV infection in human T lymphocyte cells and mononuclear phagocytic lineage cells infected with HIV comprising contacting said infected cells with a pharmaceutical preparation consisting essentially of an extract from *Salvia miltiorrhiza*, at a concentration of said extract which is effective to inhibit viral antigen expression in said HIV infected cells.

2. The method according to claim 1, wherein said contacting is carried out at a concentration of said extract from *Salvia miltiorrhiza* and for a duration which is effective to inhibit expression of HIV p24 antigen.

3. A method of inhibiting in vitro HIV infection in human T lymphocyte cells and mononuclear phagocytic lineage cells infected with HIV comprising contacting said infected cells with a pharmaceutical preparation consisting essentially of an extract from *Scutellaria baicaleusis*, at a concentration of said extract which is effective to inhibit viral antigen expression in said HIV infected cells.

4. The method of claim 3, wherein said contacting is carried out at a concentration of said extract from *Scutellaria baicaleusis* and for a duration which is effective to inhibit expression of HIV p24 antigen.

5. A method of inhibiting in vitro HIV infection in human T lymphocyte cells and mononuclear phagocytic lineage cells infected with HIV comprising contacting said infected cells with a pharmaceutical preparation consisting essentially of an extract from *Coptis chineusis*, at a concentration of said extract which is effective to inhibit viral antigen expression in said HIV infected cells.

6. The method of claim 5, wherein said contacting is carried out at a concentration of said extract from *Coptis chineusis* and for a duration which is effective to inhibit expression of HIV p24 antigen.

7. A method of inhibiting in vitro HIV infection in human T lymphocyte cells and mononuclear phagocytic lineage cells infected with HIV comprising contacting said infected cells with a pharmaceutical preparation consisting essentially of an extract from *Ligusticum wallichii*, at a concentration of said extract which is effective to inhibit viral antigen expression in said HIV infected cells.

8. The method of claim 7, wherein said contacting is carried out at a concentration of said extract from *Ligusticum wallichii* and for a duration which is effective to inhibit expression of HIV p24 antigen.

9. A method of inhibiting in vitro HIV infection in human T lymphocyte cells and mononuclear phagocytic lineage cells infected with HIV comprising contacting said infected cells with a pharmaceutical preparation consisting essentially of an extract from *Illicium lanceolatum*, at a concentration of said extract which is effective to inhibit viral antigen expression in said HIV infected cells.

10. The method of claim 9, wherein said contacting is carried out at a concentration of said extract from *Illicium lanceolatum* and for a duration which is effective to inhibit expression of HIV p24 antigen.

11. A method of inhibiting in vitro HIV infection in human T lymphocyte cells and mononuclear phagocytic lineage cells infected with HIV comprising contacting said infected cells with a pharmaceutical preparation consisting essentially of an extract from *Isatis tinctoria*, at a concentration of said extract which is effective to inhibit viral antigen expression in said HIV infected cells.

12. The method of claim 11, wherein said contacting is carried out at a concentration of said extract from *Isatis tinctoria* and for a duration which is effective to inhibit expression of HIV p24 antigen.

13. A method of inhibiting in vitro HIV infection in human T lymphocyte cells and mononuclear phagocytic lineage cells infected with HIV comprising contacting said infected cells with a pharmaceutical preparation consisting essentially of an extract from *Erycibe obtusifolia*, at a concentration of said extract which is effective to inhibit viral antigen expression in said HIV infected cells.

14. The method of claim 13, wherein said contacting is carried out at a concentration of said extract from *Erycibe obtusifolia* and for a duration which is effective to inhibit expression of HIV p24 antigen.

15. A method of inhibiting in vitro HIV infection in human T lymphocyte cells and mononuclear phagocytic lineage cells infected with HIV comprising contacting said infected cells with a pharmaceutical preparation consisting essentially of an extract from *Acanthopanax graciliatylus*, at a concentration of said extract which is effective to inhibit viral antigen expression in said HIV infected cells.

16. The method of claim 15, wherein said contacting is carried out at a concentration of said extract from *Acanthopanax graciliatylus* and for a duration which is effective to inhibit expression of HIV p24 antigen.

17. A method of inhibiting in vitro HIV infection in human T lymphocyte cells and mononuclear phagocytic lineage cells infected with HIV comprising contacting said infected cells with a pharmaceutical preparation consisting essentially of an extract from *Bostaurus domesticus*, at a concentration of said extract which is effective to inhibit viral antigen expression in said HIV infected cells.

18. The method of claim 17, wherein said contacting is carried out at a concentration of said extract from *Bostaurus domesticus* and for a duration which is effective to inhibit expression of HIV p24 antigen.

19. A method of inhibiting in vitro HIV infection in human T lymphocyte cells and mononuclear phagocytic lineage cells infected with HIV comprising contacting said infected cells with a pharmaceutical preparation consisting essentially of an extract from *Inula helenium*, at a concentration of said extract which is effective to inhibit viral antigen expression in said HIV infected cells.

20. The method of claim 19, wherein said contacting is carried out at a concentration of said extract from *Inula helenium* and for a duration which is effective to inhibit expression of HIV p24 antigen.

* * * * *